US010925476B2

(12) United States Patent
Yamamoto

(10) Patent No.: US 10,925,476 B2
(45) Date of Patent: Feb. 23, 2021

(54) ENDOSCOPIC SYSTEM AND ENDOSCOPIC SYSTEM OPERATING METHOD

(71) Applicant: FUJIFILM Corporation, Tokyo (JP)

(72) Inventor: Hiroaki Yamamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 336 days.

(21) Appl. No.: 16/038,195

(22) Filed: Jul. 18, 2018

(65) Prior Publication Data

US 2018/0317754 A1 Nov. 8, 2018

Related U.S. Application Data

(63) Continuation of application No. PCT/JP2017/001295, filed on Jan. 17, 2017.

(30) Foreign Application Priority Data

Mar. 9, 2016 (JP) .............................. JP2016-045505

(51) Int. Cl.
  *A61B 1/05* (2006.01)
  *A61B 1/00* (2006.01)
  (Continued)

(52) U.S. Cl.
  CPC ............ *A61B 1/05* (2013.01); *A61B 1/00009* (2013.01); *A61B 1/00057* (2013.01); *A61B 1/00096* (2013.01); *A61B 1/00188* (2013.01); *A61B 1/045* (2013.01); *A61B 1/0638* (2013.01); *A61B 1/0669* (2013.01); *A61B 1/0676* (2013.01); *G02B 23/243* (2013.01);
  (Continued)

(58) Field of Classification Search
  CPC . A61B 1/00057; A61B 1/00188; A61B 1/045; A61B 1/0638; A61B 1/0669; A61B 1/076; G02B 23/2423; G02B 23/243
  See application file for complete search history.

(56) References Cited

U.S. PATENT DOCUMENTS 9,172,862 B2 * 10/2015 Miyakoshi ......... H04N 5/23212
9,895,054 B2 * 2/2018 Morimoto ............ A61B 5/1459
(Continued)

FOREIGN PATENT DOCUMENTS

EP          2070469       6/2009
EP          2754379       7/2014
(Continued)

OTHER PUBLICATIONS

"International Search Report (Form PCT/ISA/210) of PCT/JP2017/001295," dated Apr. 25, 2017, with English translation thereof, pp. 1-3.
(Continued)

*Primary Examiner* — Timothy J Neal
*Assistant Examiner* — Jae Woo
(74) *Attorney, Agent, or Firm* — JCIPRNET

(57) ABSTRACT

A correction image fluctuation amount obtained in a calibration mode and a measurement image fluctuation amount obtained in a measurement mode are compared with each other. On the basis of the comparison result, a temporary correction value, which satisfies a specific condition among temporary correction values stored in the correction value storage unit, is determined as a measurement correction value to be used for correction in a correcting unit.

16 Claims, 14 Drawing Sheets

(51) Int. Cl.
*A61B 1/06* (2006.01)
*G02B 23/24* (2006.01)
*H04N 7/18* (2006.01)
*A61B 1/045* (2006.01)
*G02B 26/00* (2006.01)

(52) U.S. Cl.
CPC ..... *G02B 23/2423* (2013.01); *G02B 23/2461* (2013.01); *G02B 23/2484* (2013.01); *G02B 26/008* (2013.01); *H04N 7/18* (2013.01); *A61B 1/0005* (2013.01)

(56) References Cited

U.S. PATENT DOCUMENTS

| | | | | |
|---|---|---|---|---|
| 2002/0168096 | A1* | 11/2002 | Hakamata | A61B 1/00009 382/132 |
| 2005/0209517 | A1* | 9/2005 | Diab | A61B 5/1455 600/323 |
| 2008/0273099 | A1* | 11/2008 | Ono | H04N 5/23212 348/241 |
| 2009/0147124 | A1 | 6/2009 | Taniyama et al. | |
| 2010/0220200 | A1* | 9/2010 | Otake | H04N 5/23248 348/208.4 |
| 2012/0053434 | A1* | 3/2012 | Saito | A61B 1/063 600/324 |
| 2012/0092471 | A1* | 4/2012 | Takamatsu | A61B 1/00009 348/65 |
| 2012/0179013 | A1* | 7/2012 | Saito | A61B 1/00009 600/339 |
| 2012/0262559 | A1* | 10/2012 | On | H04N 5/23267 348/65 |
| 2013/0012794 | A1* | 1/2013 | Zeng | H04N 5/332 600/328 |
| 2013/0030268 | A1* | 1/2013 | Saito | A61B 1/05 600/325 |
| 2013/0211217 | A1* | 8/2013 | Yamaguchi | A61B 5/1459 600/327 |
| 2014/0350338 | A1* | 11/2014 | Tanaka | A61B 1/00193 600/111 |
| 2015/0208958 | A1* | 7/2015 | Kaku | A61B 1/0638 600/339 |
| 2015/0216460 | A1* | 8/2015 | Shigeta | A61B 1/05 600/339 |
| 2016/0287061 | A1* | 10/2016 | Shigeta | A61B 1/0638 |
| 2017/0014055 | A1* | 1/2017 | Otani | A61B 1/0653 |
| 2018/0160082 | A1* | 6/2018 | Koike | H04N 9/3182 |
| 2018/0271412 | A1* | 9/2018 | Shigeta | A61B 5/14552 |
| 2018/0317754 | A1* | 11/2018 | Yamamoto | A61B 1/05 |
| 2018/0333045 | A1* | 11/2018 | Yamanashi | A61B 1/00009 |
| 2019/0107707 | A1* | 4/2019 | Takahashi | A61B 1/00096 |
| 2019/0320879 | A1* | 10/2019 | Langell | A61B 1/00009 |
| 2020/0018947 | A1* | 1/2020 | Tsuyuki | H04N 5/2254 |
| 2020/0022570 | A1* | 1/2020 | Kennedy | A61B 1/00193 |

FOREIGN PATENT DOCUMENTS

| | | |
|---|---|---|
| EP | 2904956 | 8/2015 |
| JP | 2009159603 | 7/2009 |
| JP | 2012066065 | 4/2012 |
| JP | 2012217579 | 11/2012 |
| JP | 2013022341 | 2/2013 |

OTHER PUBLICATIONS

"Written Opinion of the International Searching Authority (Form PCT/ISA/237) of PCT/JP2017/001295," dated Apr. 25, 2017, with English translation thereof, pp. 1-7.

"Search Report of Europe Counterpart Application", dated Mar. 1, 2019, p. 1-p. 7.

* cited by examiner

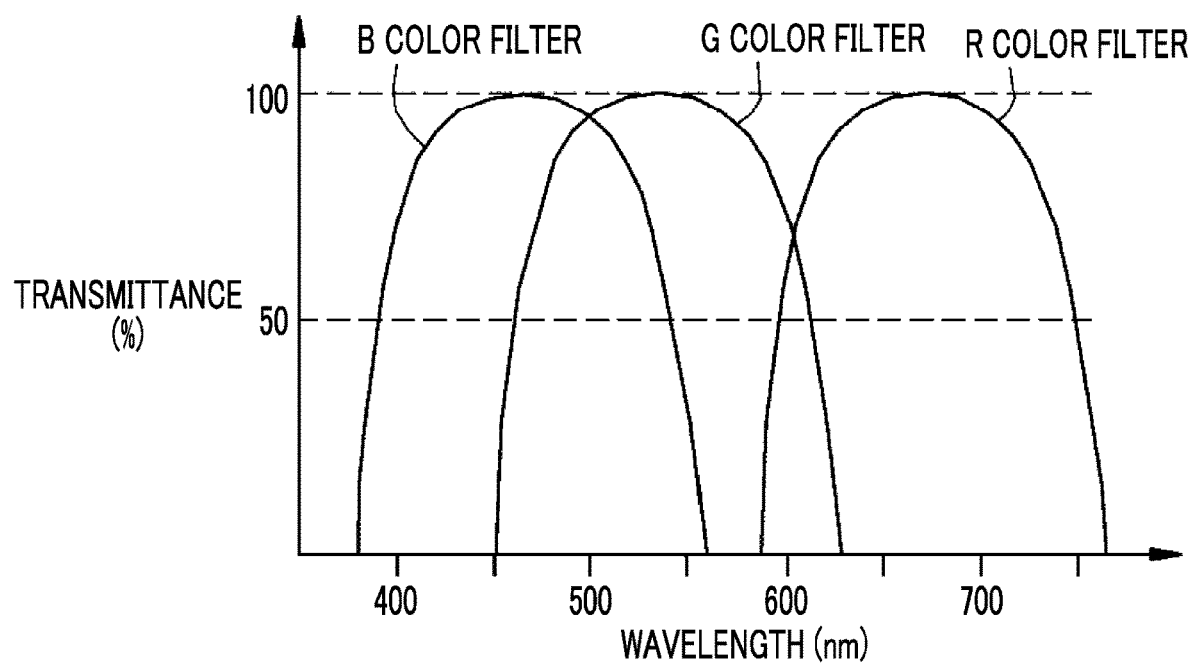

FIG. 5

| ILLUMINATION | | IMAGING (IMAGE SIGNAL) | |
|---|---|---|---|
| FIRST MEASUREMENT LIGHT EMISSION MODE | EMISSION OF SECOND BLUE LIGHT | FIRST MEASUREMENT IMAGING MODE | (B1, G1, R1) |
| SECOND MEASUREMENT LIGHT EMISSION MODE | EMISSION OF FIRST BLUE LIGHT EMISSION OF GREEN LIGHT EMISSION OF RED LIGHT | SECOND MEASUREMENT IMAGING MODE | (B2, G2, R2) |

FIG. 6

| ILLUMINATION | | IMAGING (IMAGE SIGNAL) | |
|---|---|---|---|
| FIRST CALIBRATION LIGHT EMISSION MODE | EMISSION OF FIRST BLUE LIGHT | FIRST CALIBRATION IMAGING MODE | (Bp, Gp, Rp) |
| SECOND CALIBRATION LIGHT EMISSION MODE | EMISSION OF SECOND BLUE LIGHT | SECOND CALIBRATION IMAGING MODE | (Bq, Gq, Rq) |
| THIRD CALIBRATION LIGHT EMISSION MODE | EMISSION OF GREEN LIGHT | THIRD CALIBRATION IMAGING MODE | (Br, Gr, Rr) |
| FOURTH CALIBRATION LIGHT EMISSION MODE | EMISSION OF RED LIGHT | FOURTH CALIBRATION IMAGING MODE | (Bs, Gs, Rs) |

| | CORRECTION IMAGE FLUCTUATION AMOUNT | TEMPORARY CORRECTION VALUE |
|---|---|---|
| T1 | FLUCTUATION AMOUNT X1 OF YELLOW COLORING AGENT | TEMPORARY CORRECTION VALUE AX1 FOR YELLOW COLORING AGENT |
| | ⋮ | ⋮ |
| T2 | FLUCTUATION AMOUNT X2 OF YELLOW COLORING AGENT | TEMPORARY CORRECTION VALUE AX2 FOR YELLOW COLORING AGENT |
| | ⋮ | ⋮ |
| | ⋮ | ⋮ |

FIG. 15

| | CORRECTION IMAGE FLUCTUATION AMOUNT | TEMPORARY CORRECTION VALUE | |
|---|---|---|---|
| T1 | FLUCTUATION AMOUNT X1 OF YELLOW COLORING AGENT | TEMPORARY CORRECTION VALUE AX1 FOR YELLOW COLORING AGENT | → MEASUREMENT CORRECTION VALUE FOR YELLOW COLORING AGENT |
| | POSITIONAL SHIFT AMOUNT Y1 BETWEEN FRAMES | TEMPORARY CORRECTION VALUE AY1 FOR POSITIONAL SHIFT BETWEEN FRAMES | |
| | ⋮ | ⋮ | |
| T2 | FLUCTUATION AMOUNT X2 OF YELLOW COLORING AGENT | TEMPORARY CORRECTION VALUE AX2 FOR YELLOW COLORING AGENT | MEASUREMENT CORRECTION VALUE FOR POSITIONAL SHIFT BETWEEN FRAMES |
| | POSITIONAL SHIFT AMOUNT Y2 BETWEEN FRAMES | TEMPORARY CORRECTION VALUE AY2 FOR POSITIONAL SHIFT BETWEEN FRAMES | → |
| | ⋮ | ⋮ | |
| | ⋮ | ⋮ | |

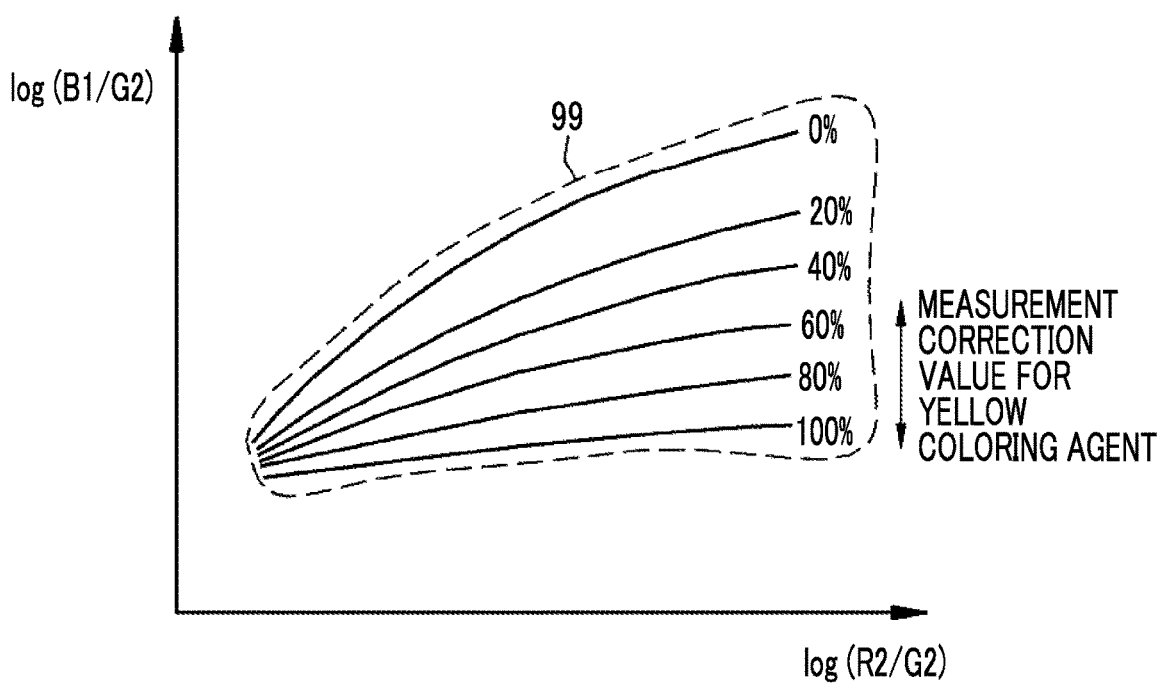

ENDOSCOPIC SYSTEM AND ENDOSCOPIC SYSTEM OPERATING METHOD

CROSS-REFERENCE TO RELATED APPLICATIONS

This application is a Continuation of PCT International Application No. PCT/JP2017/1295, filed on Jan. 17, 2017, which claims priority under 35 U.S.C. § 119(a) to Japanese Patent Application No. 2016-045505, filed on Mar. 9, 2016. Each of the above application(s) is hereby expressly incorporated by reference, in its entirety, into the present application.

BACKGROUND OF THE INVENTION

1. Field of the Invention

The present invention relates to an endoscope system and an endoscope system operating method that calculate living body characteristic amounts, such as an oxygen saturation degree of an observation target.

2. Description of the Related Art

In the medical field, it is general to perform diagnosis using endoscope systems including a light source device, an endoscope, and a processor device. Particularly, endoscope systems for obtaining an observation image in which specific tissues or structures, such as blood vessels or duct structures, are emphasized not only by simply imaging an observation target but also by devising the wavelength of illumination light to be radiated the observation target or by performing signal processing, such as spectrum estimation processing, on image signals obtained by imaging the observation target have become widespread.

Additionally, in recent years, there are also endoscope systems for obtaining living body characteristic amount information on the basis of the image signals obtained by imaging the observation target. For example, even among living body characteristic amounts, diagnosis of a lesioned site using the oxygen saturation degree of hemoglobin in blood has been performed. In JP2013-22341A (JP5426620B), calculation of the oxygen saturation degree is performed using light of a wavelength band in which light absorption coefficients of oxygenated hemoglobin and reduced hemoglobin are different from each other.

Additionally, since the calculation accuracy of the oxygen saturation degree as described above is affected by various factors, such as various parts such as the esophagus, the stomach, and the large intestine, and differences among patients such as men and women and adults and children, in JP2013-22341A (JP5426620B), pre-measurement of the oxygen saturation degree is performed before main measurement is performed. In this JP2013-22341A (JP5426620B), an oxygen saturation degree calculation table to be used for the calculation of the oxygen saturation degree is corrected on the basis of a correction value obtained from a difference between the oxygen saturation degree obtained by the pre-measurement and a predetermined reference value of the oxygen saturation degree. By performing such correction, it is possible to accurately calculate the oxygen saturation degree irrespective of various parts or the like.

SUMMARY OF THE INVENTION

The calculation accuracy of the oxygen saturation degree is affected by blurring, defocusing, or the like in image signals, in addition to differences among various parts, such as the esophagus and the stomach. Moreover, in a case where image signals equivalent to two or more frames obtained by imaging an observation target at different timings are used for the calculation processing of the oxygen saturation degree, a positional shift between frames or fluctuation of the quantity of light between frames also affect the calculation accuracy of the oxygen saturation degree.

Hence, as disclosed in JP2013-22341A (JP5426620B), even in a case where measurement is performed in a region where the reference value of the oxygen saturation degree is obtained in a case where the pre-measurement is performed, the oxygen saturation degree cannot be accurately calculated in the pre-measurement, in a case where various fluctuation factors, such as the blurring, the defocusing, the positional shift between frames, and light quantity fluctuation between frames, occur during the measurement. In this way, in a case where the oxygen saturation degree cannot be accurately calculated in the pre-measurement, the oxygen saturation degree can be accurately calculated even in the main measurement. Hence, it has been required to be able to accurately calculate living body characteristic amounts, such as the oxygen saturation degree, even in a situation where the various fluctuation factors, such as the positional shift between frames, occur.

An object of the invention is to provide is an endoscope system and an endoscope system operating method capable of accurately calculating living body characteristic amounts, such as an oxygen saturation degree, even in a situation where various fluctuation factors, such as a positional shift between frames, occur.

The invention provides an endoscope system having a living body characteristic amount calculation unit that performs living body characteristic amount calculation processing in which a living body characteristic amount is calculated on the basis of a measurement multi-frame image obtained by imaging an observation target at different timings, and a correcting unit that corrects contents of the living body characteristic amount calculation processing. The endoscope system comprises an image acquisition unit that acquires at least one set of correction multi-frame images by imaging the observation target at the different timings; a correction image fluctuation amount calculation unit that calculates a correction image fluctuation amount showing a fluctuation amount from a reference image state with respect to an image state based on each of the correction multi-frame images; a correction value calculation unit that calculates a temporary correction value, which is a candidate for a measurement correction value to be used for correction in the correcting unit, on the basis of the correction image fluctuation amount; a correction value storage unit that stores the correction image fluctuation amount and the temporary correction value in association with each other; a measurement image fluctuation amount calculation unit that calculates a measurement image fluctuation amount showing a fluctuation amount from the reference image state with respect to an image state based on the measurement multi-frame image; and a correction value determination unit that compares the correction image fluctuation amount stored in the correction value storage unit with the measurement image fluctuation amount, and determines a temporary correction value, which satisfies a specific condition among temporary correction values stored in the correction value storage unit, as the measurement correction value, on the basis of the comparison result.

It is preferable that the correction value determination unit determines a temporary correction value, which satisfies the specific condition and is associated with a correction image fluctuation amount nearest to the measurement image fluctuation amount, as the measurement correction value. It is preferable that the correction value determination unit calculates a fluctuation amount index value from the correction image fluctuation amount and the measurement image fluctuation amount, and determines a temporary correction value, which satisfies the specific condition and is associated with a correction image fluctuation amount calculated in a case where the fluctuation amount index value falls within a specific range, as the measurement correction value. It is preferable that the fluctuation amount index value is a difference between the correction image fluctuation amount and the measurement image fluctuation amount or a ratio between the correction image fluctuation amount and the measurement image fluctuation amount. It is preferable that the correction value determination unit determines a predetermined default temporary correction value as the measurement correction value in a case where there is no temporary correction value that satisfies the specific condition.

It is preferable that the correction image fluctuation amount calculation unit calculates a fluctuation amount in a correction image fluctuation amount calculation region in the correction multi-frame image as the correction image fluctuation amount, and the measurement image fluctuation amount calculation unit calculates a fluctuation amount in a measurement image fluctuation amount calculation region in the measurement multi-frame image as the measurement image fluctuation amount. It is preferable that the correction value determination unit performs comparison between the correction image fluctuation amount and the measurement image fluctuation amount in a region where the correction image fluctuation amount calculation region and the measurement image fluctuation amount calculation region overlap each other.

It is preferable that the correction image fluctuation amount calculation unit calculates correction image fluctuation amounts, respectively, for a plurality of types of fluctuation factors that cause fluctuation with respect to the reference image state, the measurement image fluctuation amount calculation unit calculates measurement image fluctuation amounts, respectively, for the plurality of types of fluctuation factors that cause fluctuation with respect to the reference image state, and the correction value determination unit compares the correction image fluctuation amounts with the measurement image fluctuation amounts for each type of fluctuation factor. It is preferable that the fluctuation factors are a positional shift between the correction multi-frame images, a positional shift between the measurement multi-frame images, movements within the correction multi-frame image, a movement within the measurement multi-frame image, a change in a light emission amount of illumination light in a case where the correction multi-frame images are acquired, a change in a light emission amount of illumination light in a case where the measurement multi-frame image is acquired, changes in pixel values of the correction multi-frame images, changes in pixel values of the measurement multi-frame images, a change in the amount of a residual liquid in the correction multi-frame images, or a change in the amount of a residual liquid in the measurement multi-frame image. It is preferable that the correcting unit performs at least any of correction of a calculation table to be used for the calculation of the living body characteristic amount, correction based on the measurement multi-frame image, or correction of the living body characteristic amount, as the correction of the contents of the living body characteristic amount calculation processing.

The invention provides an endoscope system operating method having performing living body characteristic amount calculation processing in which a living body characteristic amount is calculated on the basis of a measurement multi-frame image obtained by imaging an observation target at different timings, by a living body characteristic amount calculation unit and correcting contents of the living body characteristic amount calculation processing, by a correcting unit. The method comprises acquiring at least one set of correction multi-frame images by imaging the observation target at the different timings, by an image acquisition unit; calculating a correction image fluctuation amount showing a fluctuation amount from a reference image state with respect to an image state based on each of the correction multi-frame images, by a correction image fluctuation amount calculation unit; calculating a temporary correction value, which is a candidate for a measurement correction value to be used for correction in the correcting unit, on the basis of the correction image fluctuation amount, by a correction value calculation unit; storing the correction image fluctuation amount and the temporary correction value in association with each other in a correction value storage unit, by an associating unit; calculating a measurement image fluctuation amount showing a fluctuation amount from the reference image state with respect to an image state based on the measurement multi-frame image, by a measurement image fluctuation amount calculation unit; and comparing the correction image fluctuation amount stored in the correction value storage unit with the measurement image fluctuation amount, and determining a temporary correction value, which satisfies a specific condition among temporary correction values stored in the correction value storage unit, as the measurement correction value, on the basis of the comparison result, by a correction value determination unit.

According to the invention, it is possible to accurately calculate living body characteristic amounts, such as an oxygen saturation degree, even in a situation where various fluctuation factors, such as a positional shift between frames, occur.

BRIEF DESCRIPTION OF THE DRAWINGS

FIG. 3 is a graph illustrating the spectral sensitivity of an imaging sensor.

FIG. 4 is an explanatory view illustrating light emission of illumination light and imaging of an observation target in a normal mode.

FIG. 5 is an explanatory view illustrating light emission of the illumination light and imaging of the observation target in an oxygen saturation degree mode.

FIG. 6 is an explanatory view illustrating light emission of the illumination light and imaging of the observation target in an in a calibration mode.

FIG. 15 is an explanatory view illustrating a method for determining a measurement correction value.

FIG. 16 is an explanatory view illustrating correction of an oxygen saturation degree calculation table.

DESCRIPTION OF THE PREFERRED EMBODIMENTS

First Embodiment

Figure 1:
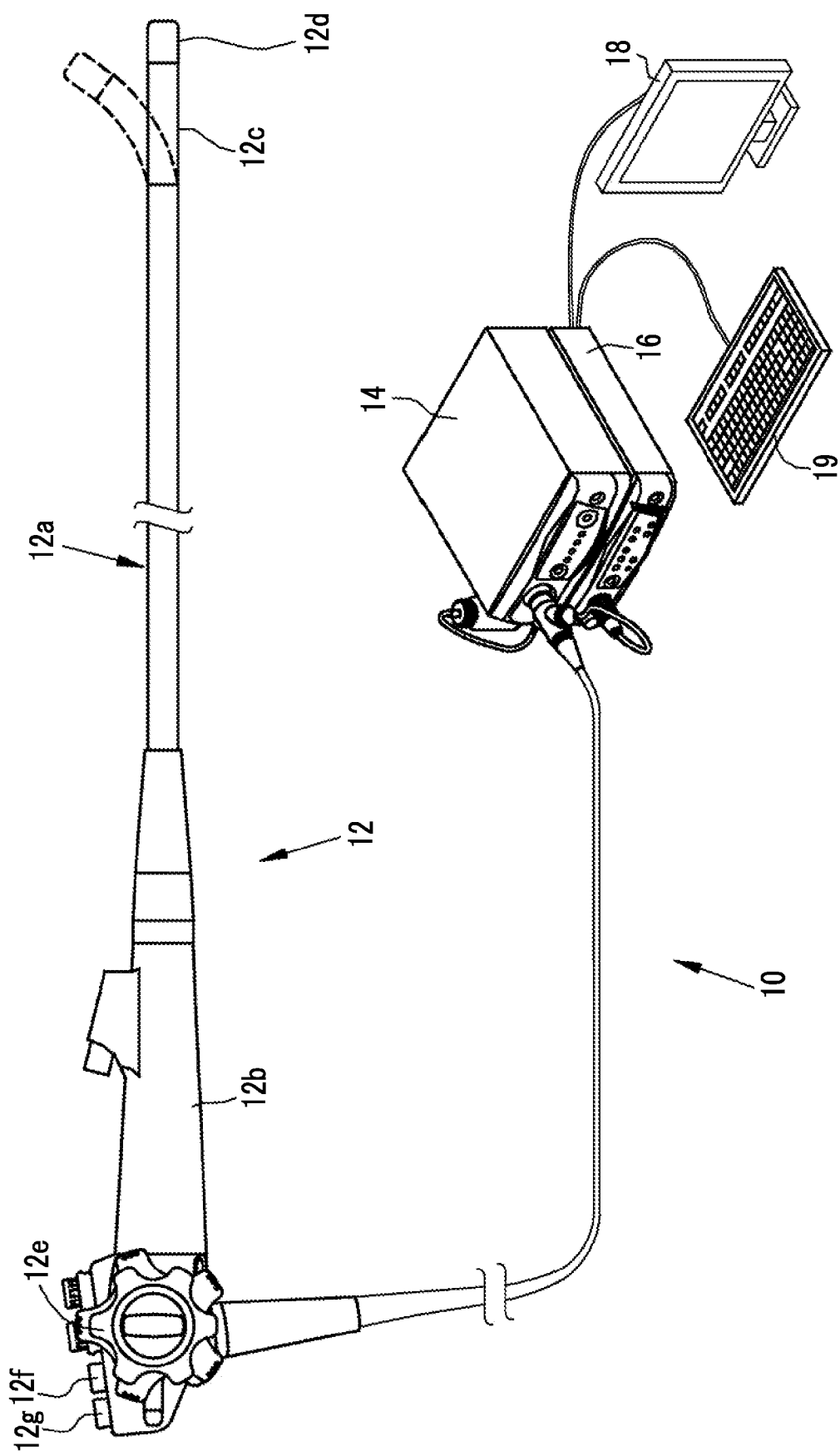
FIG. 1 is an external view of an endoscope system.

In FIG. 1, an endoscope system 10 has an endoscope 12, a light source device 14, a processor device 16, a monitor 18, and a console 19. The endoscope 12 is optically connected to the light source device 14 and is electrically connected to the processor device 16. The endoscope 12 has an insertion part 12a to be inserted into the body of an observation target, an operating part 12b provided at a base end portion of the insertion part 12a, and a bending part 12c and a distal end part 12d provided on a distal end side of the insertion part 12a. By operating an angle knob 12e of the operating part 12b, the bending part 12c makes a bending motion. The distal end part 12d is directed in a desired direction by this bending motion of the bending part 12c. In addition, the distal end part 12d is provided with a jet port (not illustrated) that jet a cleaning liquid toward the observation target.

Additionally, the operating part 12b is provided with a mode switchover switch (mode switchover SW) 12f used for a switching operation in an observation mode and a still image acquisition instruction unit 12g used for an instruction for acquiring a still image of the observation target, in addition to the angle knob 12e.

The endoscope system 10 has three observation modes of a normal mode, an oxygen saturation degree mode ("measurement mode"), and a calibration mode. In the normal mode, a natural-tone image (hereinafter, referred to as a normal image) obtained by imaging the observation target using white light for illumination light is displayed on the monitor 18. In the oxygen saturation degree mode, the oxygen saturation degree of the observation target is calculated, and an image (hereinafter referred to as an oxygen saturation degree image) obtained by imaging the calculated oxygen saturation degree in pseudo-colors or the like is displayed on the monitor 18. In the calibration mode, a correction value to be used for correction for improving the calculation accuracy of the oxygen saturation degree is acquired.

The processor device 16 is electrically connected to the monitor 18 and the console 19. The monitor 18 outputs and displays the image of the observation target, information accompanying the image of the observation target, and the like. The console 19 functions as a user interface that receives an input operation, such as function setting. In addition, an external recording unit (not illustrated) that records an image, image information, and the like may be connected to the processor device 16.

Figure 2:
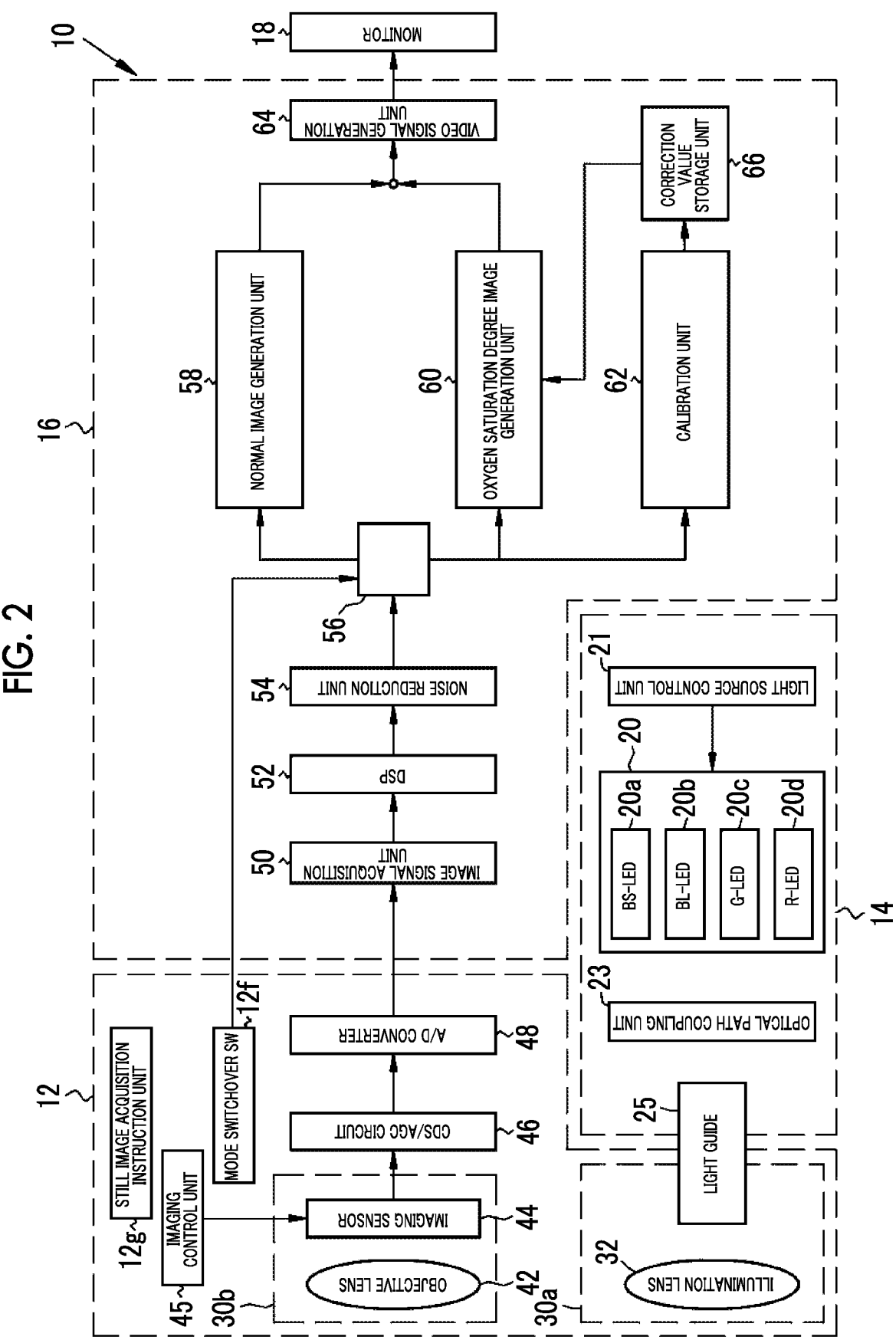
FIG. 2 is a block diagram illustrating the functions of the endoscope system of the first embodiment.

In FIG. 2, the light source device 14 includes a light source 20, and a light source control unit 21 that controls the light source 20. The light source 20 has, for example, a plurality of semiconductor light sources, switches on or off these semiconductor light sources, respectively, and emits illumination light for illuminating the observation target by controlling the light emission amounts of the respective semiconductor light sources in a case where the semiconductor light sources are switched on. The light source 20 has four color LEDs of a blue short-wavelength light emitting diode (BS-LED) 20a, a blue long-wavelength light emitting diode (BL-LED) 20b, a green light emitting diode (G-LED) 20c, and a red light emitting diode (R-LED) 20d.

The BS-LED 20a emits first blue light BS having a wavelength band of 450±10 nm. The BL-LED 20b emits second blue light BL having a wavelength band of 470±10 nm. The G-LED 20c emits green light G having a wavelength band of 540±10 nm. The R-LED 20d emits red light R having a wavelength band of 640±20 nm. In addition, center wavelengths and peak wavelengths in the LEDs 20a to 20d may be the same as each other or may be different from each other.

The light source control unit 21 independently controls switching-on or switching-off of the LEDs 20a to 20d, light emission amounts during switching on, and the like by independently inputting control signals to the LEDs 20a to 20d. Switching-on or switching-off control in the light source control unit 21 varies in the respective modes. In the normal mode, the first blue light BS, the green light G, and the red light R are simultaneously emitted by simultaneously switching on the BS-LED 20a, the G-LED 20c, and the R-LED 20d. In the oxygen saturation degree mode, a first measurement light emission mode where the second blue light BL is emitted by switching on the BL-LED 20b, and a second measurement light emission mode where the first blue light BS, the green light G, and the red light R are simultaneously emitted by simultaneously switching on the BS-LED 20a, the G-LED 20c, and the R-LED 20d are alternately repeated.

In the calibration mode, the first blue light BS, the second blue light BL, the green light G, and the red light R are sequentially emitted by sequentially switching on the BS-LED 20a, the BL-LED 20b, the G-LED 20c, and the R-LED 20d. In this calibration mode, a mode where the first blue light BS is emitted is defined as a first calibration light emission mode, a mode where the second blue light BL is emitted is defined as a second calibration light emission mode, a mode where the green light G is emitted is defined as a third calibration light emission mode, and a mode where the red light R is emitted is defined as a fourth calibration light emission mode.

The lights emitted from the respective LEDs 20a to 20d enter a light guide 25 via an optical-path coupling unit 23 composed of a mirror, a lens, and the like. The light guide 25 is built in the endoscope 12 and a universal cord (a cord that connects the endoscope 12, and the light source device 14 and the processor device 16 together). The light guide 25 propagates the light from the respective LEDs 20a to 20d, to the distal end part 12d of the endoscope 12.

The distal end part 12d of the endoscope 12 is provided with an illumination optical system 30a and an imaging optical system 30b. The illumination optical system 30a has an illumination lens 32, and the illumination light propagated by the light guide 25 is radiated to the observation target via the illumination lens 32. The imaging optical system 30b has an objective lens 42 and an imaging sensor 44. The light from the observation target to which the illumination light has been radiated enters the imaging sensor 44 via the objective lens 42. Accordingly, the image of the observation target is formed on the imaging sensor 44.

The imaging sensor 44 is a color imaging sensor that images the observation target under illumination with the illumination light. Each pixel of the imaging sensor 44 is provided with any of a blue pixel (B pixel) having a blue (B) color filter, a green pixel (G pixel) having a green (G) color filter, a red pixel (R pixel) having a red (R) color filter. As illustrated in FIG. 3, the B color filter allows mainly blue band light, specifically, light in a wavelength band of 380 to 560 nm to be transmitted therethrough. A peak wavelength at which the transmittance becomes maximum is present in the vicinity of 460 to 470 nm. The G color filter allows mainly green band light, specifically, light in a wavelength band of 450 to 630 nm to be transmitted therethrough. The R color filter allows mainly red band light, specifically, light 580 to 760 nm to be transmitted therethrough.

As the imaging sensor 44, a charge coupled device (CCD) imaging sensor or a complementary metal-oxide semiconductor (CMOS) imaging sensor is available. Additionally, instead of the primary color imaging sensor 44, a complementary color imaging sensor including complementary color filters in C (cyan), M (magenta), Y (yellow), and G (green) may be used. In a case where the complementary color imaging sensor is used, image signals in four colors of CMYG are output. Thus, image signals in respective colors of RGB that are the same colors as those of the imaging sensor 44 can be obtained by converting the image signals in four colors of CMYG into the image signals in three colors of RGB through color conversion of complementary color to primary color.

Driving of the imaging sensor 44 is controlled by an imaging control unit 45. The control in the imaging control unit 45 varies in the respective modes. As illustrated in FIG. 4, in the normal mode, the imaging control unit 45 controls the imaging sensor 44 so as to image the observation target under illumination for each frame with the first blue light BS, the green light G, and the red light R. As a result, a Bc image signal is output from the B pixel of the imaging sensor 44, a Gc image signal is output from the G pixel, and an Rc image signal is output from the R pixel.

As illustrated in FIG. 5, in the oxygen saturation degree mode, the imaging sensor 44 controls the imaging control unit 45 so as to alternately repeat a first measurement imaging mode where the observation target under illumination is imaged by one frame with the second blue light BL in the first measurement light emission mode, and a second measurement imaging mode where the observation target under illumination is imaged by one frame with the first blue light BS, the green light G, and the red light R in the second measurement light emission mode. Accordingly, in the first measurement imaging mode, a B1 image signal is output from the B pixel of the imaging sensor 44, a G1 image signal is output from the G pixel, and an R1 image signal is output from the R pixel. In the second measurement imaging mode, a B2 image signal is output from the B pixel of the imaging sensor 44, a G2 image signal is output from the G pixel, and an R2 image signal is output from the R pixel.

As illustrated in FIG. 6, in the calibration mode, the imaging control unit 45 controls the imaging sensor 44 so as to sequentially perform a first calibration imaging mode where the observation target under illumination is imaged by one frame with first blue light BS in the first calibration light emission mode, a second calibration imaging mode where the observation target under illumination is imaged by one frame with the second blue light BL in the second calibration light emission mode, a third calibration imaging mode where the observation target under illumination is imaged by one frame with the green light G in the third calibration light emission mode, and a fourth calibration imaging mode where the observation target under illumination is imaged by one frame with the red light R in the fourth calibration light emission mode.

Accordingly, in the first calibration imaging mode, a Bp image signal is output from the B pixel of the imaging sensor 44, a Gp image signal is output from the G pixel, and an Rp image signal is output from the R pixel. Additionally, in the second calibration imaging mode, a Bq image signal is output from the B pixel of the imaging sensor 44, a Gq image signal is output from the G pixel, and an Rq image signal is output from the R pixel. Additionally, in the third calibration imaging mode, a Br image signal is output from the B pixel of the imaging sensor 44, a Gr image signal is output from the G pixel, and an Rr image signal is output from the R pixel. Additionally, in the fourth calibration imaging mode, a Bs image signal is output from the B pixel of the imaging sensor 44, a Gs image signal is output from the G pixel, and an Rs image signal is output from the R pixel.

As illustrated in FIG. 2, a correlated double sampling/automatic gain control (CDS/AGC) circuit 46 performs correlation double sampling (CDS) and automatic gain control (AGC) on analog image signals obtained from the imaging sensor 44. The image signals that have passed through the CDS/AGC circuit 46 are converted into digital image signals by an analog/digital (A/D) converter 48. The digital image signals after the A/D conversion are input to the processor device 16.

The processor device 16 includes an image signal acquisition unit 50, a digital signal processor (DSP) 52, a noise reduction unit 54, an image processing switching unit 56, a normal image generation unit 58, an oxygen saturation degree image generation unit 60, a calibration unit 62, and a video signal generation unit 64. The image signal acquisition unit 50 (corresponding to an "image acquisition unit") receives the image signals input from the endoscope 12 and transmits the received image signals to the DSP 52. For example, the processor device 16 has a central processing unit (CPU), and the CPU functions as the image signal acquisition unit 50, the noise reduction unit 54, the image processing switching unit 56, the normal image generation unit 58, the oxygen saturation degree image generation unit 60, the calibration unit 62, and the video signal generation unit 64.

The DSP 52 performs various kinds of signal processing, such as defect correction processing, offset processing, gain correction processing, linear matrix processing, gamma conversion processing, demosaic processing, and YC conversion processing, on the received image signals. In the defect correction processing, a signal of a defective pixel of the imaging sensor 44 is corrected. In the offset processing, a dark current component is removed from an image signal subjected to the defect correction processing, and an accurate zero level is set. In the gain correction processing, a signal level of each image signal is adjusted by multiplying an image signal of each color after the offset processing by a specific gain. The linear matrix processing for enhancing color reproducibility is performed on the image signal of each color after the gain correction processing.

Then, the brightness and the saturation of each image signal are adjusted by the gamma conversion processing. The demosaic processing (also referred to as equalization processing or synchronization processing) is performed on the image signal after the linear matrix processing, and a signal of a missing color of each pixel is created by interpolation. By means of the demosaic processing, all pixels have signals of respective RGB colors. The DSP 52 performs the YC conversion processing on each image signal after the demosaic processing, and outputs a luminance signal Y, a color difference signal Cb, and a color difference signal Cr to the noise reduction unit 54.

The noise reduction unit 54 performs noise reduction processing using, for example, a moving average method, a median filter method, or the like on the image signal subjected to the demosaic processing or the like by the DSP 52. The image signal from which noise is reduced is input to the image processing switching unit 56.

The image processing switching unit 56 switches a transmission destination of the image signal from the noise reduction unit 54 to any of the normal image generation unit 58, the oxygen saturation degree image generation unit 60, and the calibration unit 62, depending on a set mode. Specifically, in a case where the normal mode is set, the image signal from the noise reduction unit 54 is input to the normal image generation unit 58. Additionally, in a case where the oxygen saturation degree mode is set, the image signal from the noise reduction unit 54 is input to the oxygen saturation degree image generation unit 60. Additionally, in a case where the calibration mode is set, the image signal from the noise reduction unit 54 is input to the calibration unit 62.

The normal image generation unit 58 operates in a case where the normal mode is set, and further performs color conversion processing, such as 3×3 matrix processing, grayscale conversion processing, or three-dimensional look-up table (LUT) processing, on the Rc image signal, the Gc image signal, and the Bc image signal equivalent to one input frame. Then, various kinds of color emphasis processing are performed on RGB image data subjected to the color conversion processing. Structure emphasis processing, such as spatial frequency emphasis, is performed on the RGB image data subjected to the color emphasis processing. The RGB image data subjected to the structure emphasis processing is input to the video signal generation unit 64 as a normal image.

The oxygen saturation degree image generation unit 60 calculates the oxygen saturation degree using measurement multi-frame image signals (corresponding to a "measurement multi-frame image") obtained by performing illumination and imaging at different timings in the oxygen saturation degree mode. The B1 image signal obtained in the first measurement light emission mode and the imaging mode, the G2 image signal and the R2 image signal obtained in the second measurement light emission mode and the imaging mode are included in the measurement multi-frame image signals. Additionally, in the oxygen saturation degree image generation unit 60, the oxygen saturation degree is accurately calculated irrespective of a plurality of fluctuation factors, such as image blurring, by performing calculation using a measurement correction value for correcting a calculation error of the oxygen saturation degree caused by differences among parts of the observation target or patients, the influence of the yellow coloring agent, image blurring, and the like. A method for calculating the oxygen saturation degree by the oxygen saturation degree image generation unit 60 will be described below. The oxygen saturation degree image in which the calculated oxygen saturation degree is imaged with a pseudo-color or the like is generated. This oxygen saturation degree image is input to the video signal generation unit 64.

The calibration unit 62 is operated in the calibration mode before the oxygen saturation degree mode is performed, and acquires at least one set of correction multi-frame image signals (corresponding to a "correction multi-frame image") obtained by performing illumination and imaging at different timings in the calibration mode. In the calibration unit 62, a temporary correction value that may be a candidate for the measurement correction value to be used in the oxygen saturation degree mode is calculated for each correction multi-frame image signal, and a correction image fluctuation amount is calculated. Then, the calibration unit 62 associates the calculated temporary correction value with the correction image fluctuation amount of the correction multi-frame image corresponding to this temporary correction value, and stores the associated temporary correction value and correction image fluctuation amount in a correction value storage unit 66. The details of the above calibration unit 62 will be described below.

In addition, the Bp image signal obtained in the first calibration light emission mode and the imaging mode, the Bq image signal obtained in the second calibration light emission mode and the imaging mode, the Gr image signal obtained in the third calibration light emission mode and the imaging mode, and the Rs image signal obtained in the fourth calibration light emission mode and the imaging mode are included in the correction multi-frame image signals.

The video signal generation unit 64 converts image data on the normal image from the normal image generation unit 58 or image data on the oxygen saturation degree image from the oxygen saturation degree image generation unit 60 into video signals that enables full color display on the monitor 18. The converted video signals are input to the monitor 18. Accordingly, the normal image or the oxygen saturation degree image is displayed on the monitor 18.

Next, the details of the oxygen saturation degree image generation unit 60 and the calibration unit 62 will be described. The temporary correction value and the correction image fluctuation amount are calculated in the calibration unit 62. Thereafter, in the oxygen saturation degree image generation unit 60, a temporary correction value associated with the smallest correction image fluctuation amount is used as the measurement correction value. Thus, first, the calibration unit 62 will be described, and then, the oxygen saturation degree image generation unit 60 will be described.

Figures 7, 8:
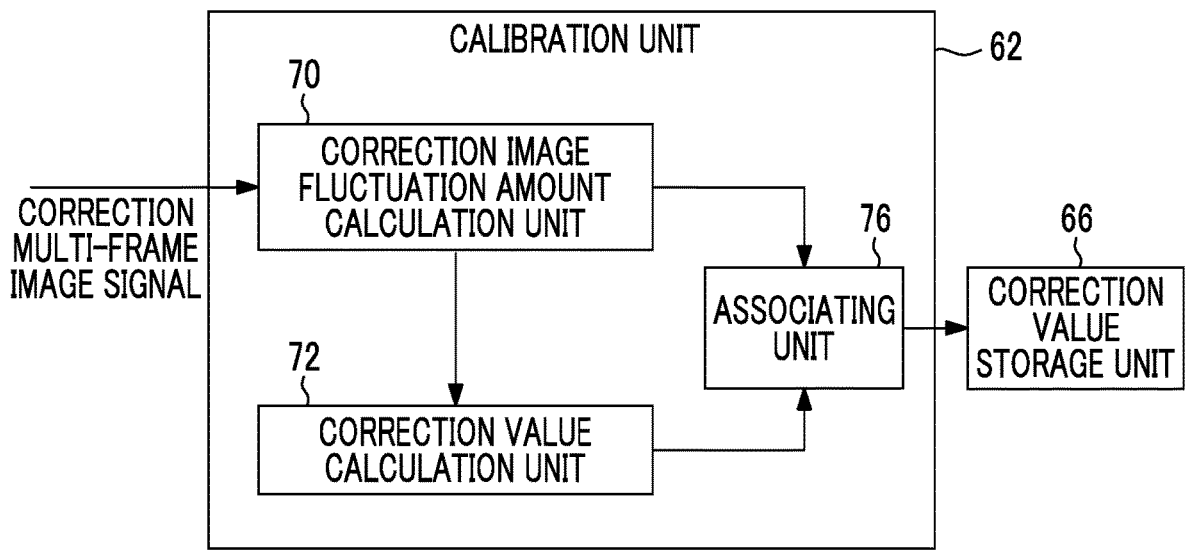
FIG. 7 is a block diagram illustrating the functions of a calibration unit.
FIG. 8 is an explanatory view indicating information to be stored in a correction value storage unit.

As illustrated in FIG. 7, the calibration unit 62 includes a correction image fluctuation amount calculation unit 70, a correction value calculation unit 72, and an associating unit 76. The correction image fluctuation amount calculation unit 70 calculates the correction image fluctuation amount from the Bp image signal, the Bq image signal, the Gr image signal, and the Rs image signal that are the correction multi-frame image signals. A specific example of a method for calculating the correction image fluctuation amount will be described below. Here, the correction image fluctuation amount shows how much an image state based on the correction multi-frame image signals fluctuates from a reference image state due to various fluctuation factors, such as a positional shift between frames.

The image state means, for example, a pixel value of any image signal of the correction multi-frame image signals, and means the magnitude of a calculated value (for example, a signal ratio or the like) obtained by calculation in which the correction multi-frame image signals are combined. Additionally, the reference image state means an image state based on an image signal obtained under a situation where various fluctuation factors are not present or are hardly present, such as no or little positional shift between frames. From the above, the correction image fluctuation amount is expressed by, for example, a difference, a ratio, or the like between the image state based on the correction multi-frame image signals and the reference image state. In addition, at least one set of the correction multi-frame image signals are input to the correction image fluctuation amount calculation unit 70, and calculation of the correction image fluctuation amount is performed for each input correction multi-frame image signal.

The fluctuation factors include a positional shift between the correction multi-frame image signals, movements within the correction multi-frame image signals, changes in the light emission amount of the illumination light in a case where the correction multi-frame image signals are acquired, changes in the pixel values of the correction multi-frame image signals, changes in the amount of a residual liquid in the correction multi-frame image signals, and the like.

Hence, the correction image fluctuation amount generated due to the above fluctuation factors includes the amount of movement between the correction multi-frame image signals, the amount of movement within any image signal of the correction multi-frame image signals, the light emission amount of illumination light in a case where the correction multi-frame image signals are obtained, respective pixel values of the correction multi-frame image signals, the amount of a residual liquid on the observation target in a case where the correction multi-frame image signals are obtained, or the like. In the correction image fluctuation amount calculation unit 70, all or some of the above correction image fluctuation amounts may be calculated.

Additionally, in the correction image fluctuation amount calculation unit 70, in the correction multi-frame image signals, the correction image fluctuation amount may be calculated in all pixel regions, or some pixel regions may be set as a correction image fluctuation amount calculation region and the correction image fluctuation amount may be calculated within the set correction image fluctuation amount calculation region. The setting of the correction image fluctuation amount calculation region may be performed for each image signal of the correction multi-frame image signals, and may be performed on only any image signal (for example, an image signal of which the correction image fluctuation amount is marked).

Additionally, in a case where the correction image fluctuation amount is calculated in the correction image fluctuation amount calculation region, the setting of the pixel regions may be performed by a user interface (UI), such as the console 19. Additionally, in the correction multi-frame image signals, a region where the correction image fluctuation amount is large may be automatically discriminated by image analysis, and the correction image fluctuation amount of the automatically discriminated region may be calculated. In addition, in the present embodiment, in order to calculate the correction image fluctuation amount or the like of the yellow coloring agent, correction multi-frame image signals equivalent to four frames are used. However, the number of frames of the correction multi-frame image may be increased or decreased in conformity with the type and the number of correction image fluctuation amounts to calculates.

The correction value calculation unit 72 calculates the temporary correction value on the basis of the correction image fluctuation amount obtained by the correction image fluctuation amount calculation unit 70. The calculation of the temporary correction value is performed for each correction image fluctuation amount calculated by the correction image fluctuation amount calculation unit 70, that is, for each correction multi-frame image signal. A specific example of a method for calculating the temporary correction value will be described below. The associating unit 76 associates the correction image fluctuation amount calculated by the correction image fluctuation amount calculation unit 70 with the temporary correction value calculated on the basis of this correction image fluctuation amount, and stores the associated correction image fluctuation amount and temporary correction value in the correction value storage unit 66.

For example, in the correction value storage unit 66, as illustrated in FIG. 8, a fluctuation amount X1 of the yellow coloring agent obtained from a correction multi-frame image signal acquired at a first timing T1 (described as "T1" in FIG. 8, the same applies below) during the calibration mode and a temporary correction value AX1 for the yellow coloring agent for this fluctuation amount is stored, and a fluctuation amount X2 of the yellow coloring agent acquired at a second timing T2 (described as "T2" in FIG. 8, the same applies below) after the first timing T1 during the calibration mode and a temporary correction value AX2 for the yellow coloring agent for this fluctuation amount is stored. In addition, not only the correction multi-frame image signals at the first timing T1 and the second timing T2 but also a correction image fluctuation amount obtained from the correction multi-frame image signals at these different timings and its temporary correction value may be stored in the correction value storage unit 66. Additionally, in addition to or instead of the fluctuation amount of the yellow coloring agent and its temporary correction value, other correction image fluctuation amounts and their temporary correction values may be stored in the correction value storage unit 66.

In the following, a method for calculating the fluctuation amount of the yellow coloring agent and a method for calculating the temporary correction value for the yellow coloring agent based on the basis of the fluctuation amount of the yellow coloring agent will be described as an example of the method for calculating the correction image fluctuation amount and the method for calculating the temporary correction value. First, the correction image fluctuation amount calculation unit 70 has information on the yellow coloring agent in the living body, and calculates living body internal information that is not affected by the oxygen saturation degree. Specifically, the signal ratio Bp/Gr of the Bp image signal and the Gr image signal is calculated for each pixel, the signal ratio Bq/Gr of the Bq image signal and the Gr image signal is calculated for each pixel, and the signal ratio Rs/Gr of the Rs image signal and the Gr image signal is calculated for each pixel.

Figure 9:
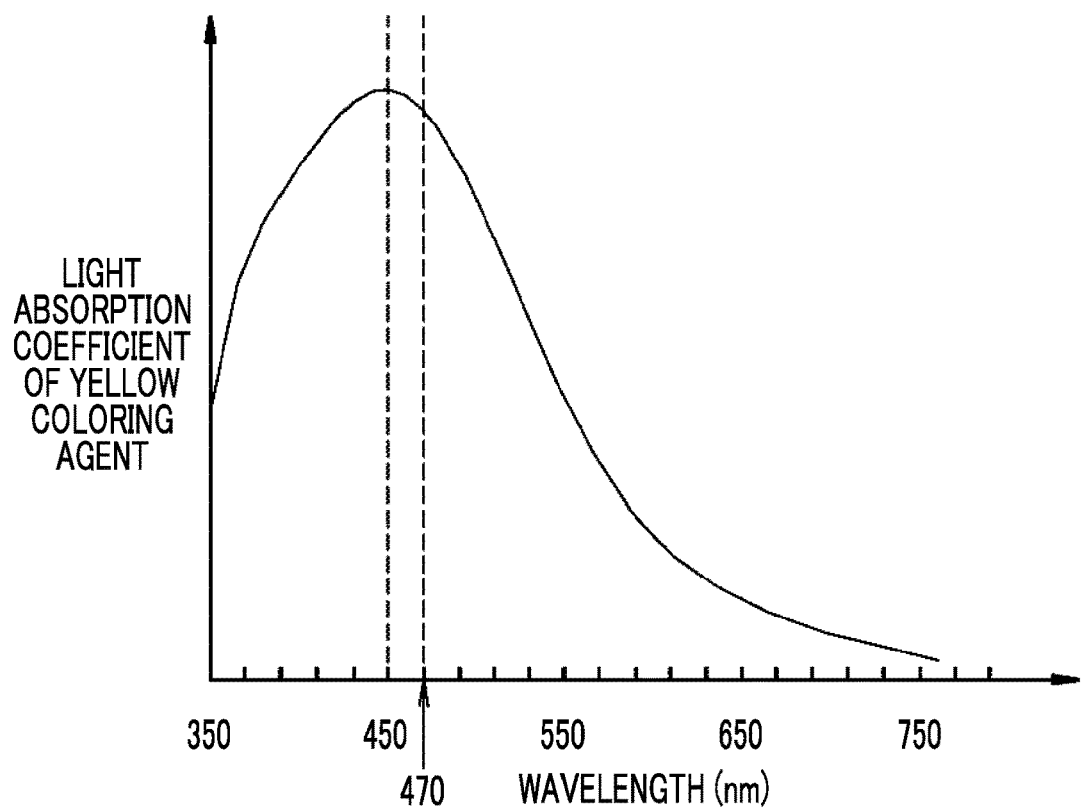
FIG. 9 is a graph illustrating the light absorption coefficient of a yellow coloring agent.

Here, Bp of the signal ratio Bp/Gr is an image signal corresponding to the first blue light BS. The wavelength band of 450±10 nm of the first blue light BS belongs to a blue band where the light absorption coefficient of hemoglobin is relatively high, and has an equal absorption wavelength where the light absorption coefficients of the oxygenated hemoglobin and the reduced hemoglobin are the same (refer to FIG. 13). Additionally, the wavelength band of 450±10 nm of the first blue light BS, as illustrated in FIG. 9, is a wavelength band where the light absorption amount easily varies according to the density of the yellow coloring agent because the wavelength band has an absorption peak wavelength where the light absorption coefficient of the yellow coloring agent is highest. Hence, in the signal ratio Bp/Gr, signal values do not vary depending on the oxygen saturation degree, but the signal values vary depending on the density of the yellow coloring agent or the amount of blood. In addition, since the wavelength band of 540±20 nm of the green light included in the Gr image signal is a wavelength band where the light absorption amount easily varies depending on the amount of blood, as described above.

Bq of the signal ratio Bq/Gr is an image signal corresponding to the second blue light BL. Since the wavelength band of 470±10 nm of the second blue light BL, as described above, belongs to a blue band where the light absorption coefficient of hemoglobin is relatively high, and has different absorption wavelengths where the light absorption coefficients of the oxygenated hemoglobin and the reduced hemoglobin are different from each other (refer to FIG. 13), the wavelength band is a wavelength band where the light absorption amount easily varies depending on the oxygen saturation degree of hemoglobin. Additionally, the center wavelength of 470 nm of the second blue light BL has a larger absorption coefficient than the other wavelength bands (refer to FIG. 13), though the absorption coefficient becomes slightly low from the absorption peak wavelength of the yellow coloring agent. Hence, in the signal ratio Bq/Gr, signal values vary depending on the oxygen saturation degree, the density of the yellow coloring agent, and the amount of blood. In contrast, in the signal ratio Rs/Gr, signal values hardly vary depending on the oxygen saturation degree and the density of the yellow coloring agent, but the signal values vary depending on the amount of blood.

Next, $\phi$ is adjusted such that a calculated value M obtained by the following Equation A becomes constant even in a case where the oxygen saturation degree varies. Information consisting of the calculated value M after this $\phi$ adjustment and the signal ratio Rs/Gr is defined as the living body internal information. This living body internal information is information that varies according to the density of the yellow coloring agent, and is information that does not vary depending on the oxygen saturation degree.

Figure 10:
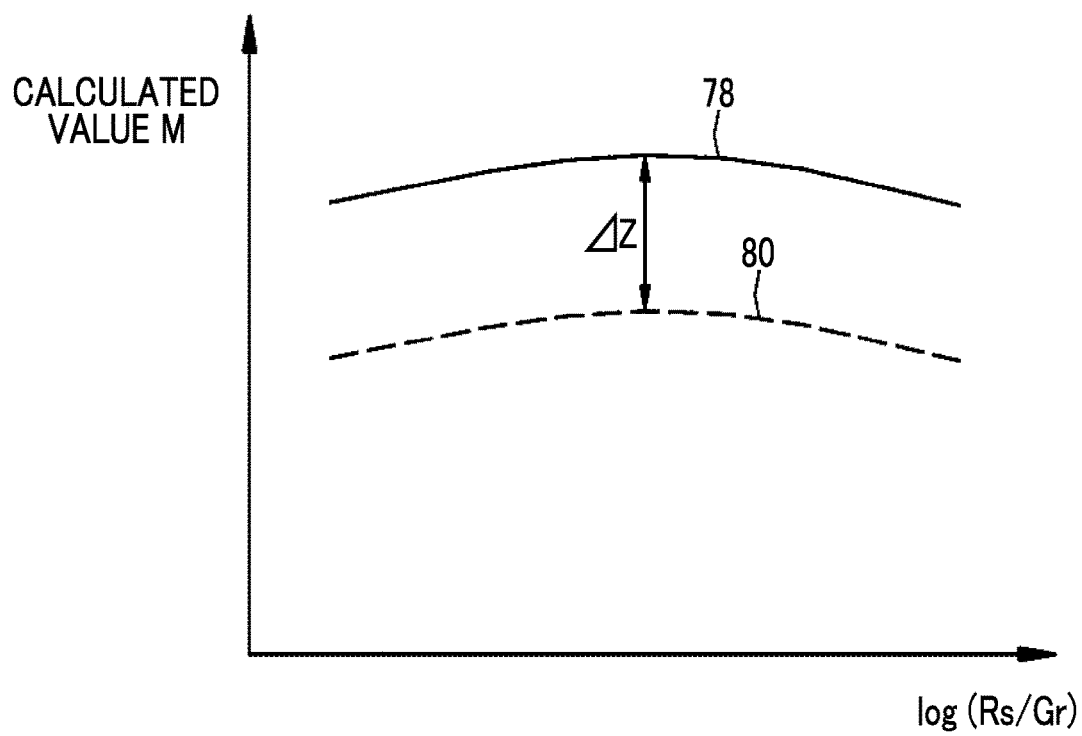
FIG. 10 is a graph illustrating the positions of a reference line and an actual measurement line in a feature space M in which a vertical axis represents a calculated value M and a horizontal axis represents Log (Rs/Gr).

Calculated value $M$=Signal ratio $Bp/Gr \times \cos\phi$−Signal ratio $Bq/Gr \times \sin\phi$. Equation A Here, in a case where a vertical axis represents, on a feature space M formed by the calculated value M based on Equation (A), preset reference information, which is obtained in a state where there is no yellow coloring agent and does not change depending on the oxygen saturation degree, and the above living body internal information, the distribution as illustrated in FIG. 10 is obtained. As illustrated in FIG. 10, a reference line 78 showing the distribution of the reference information with no influence of the yellow coloring agent, and an actual measurement line 80 on which the living body internal information affected by the yellow coloring agent is distributed are formed substantially in a horizontal axis direction, respectively. The actual measurement line 80 is an equal density line on which the density of the yellow coloring agent is the same. Additionally, in the feature space M, the reference line 78 is located above the actual measurement line 80. Additionally, in the feature space M, as the influence of the yellow coloring agent becomes larger, the actual measurement line 80 is located lower and the difference between the reference line 78 and the actual measurement line 80 becomes larger. Hence, the correction image fluctuation amount calculation unit 70 calculates a difference ΔZ between the reference line 78 and the actual measurement line 80 as the fluctuation amount of the yellow coloring agent.

The correction value calculation unit 72 calculates the temporary correction value by multiplying the fluctuation amount of the yellow coloring agent calculated by the correction image fluctuation amount calculation unit 70 by a conversion coefficient α associated with a correction aspect in a correcting unit 93 (Temporary correction value=Difference ΔZ×Coefficient α). In the correction performed by the correcting unit 93, there are three patterns including correction of the signal ratio B1/G2 and correction of the signal ratio R2/G2, which are used by an oxygen saturation degree calculation unit 88, and correction of the oxygen saturation degree calculated by the oxygen saturation degree calculation unit 88. Therefore, the above conversion coefficient α also has three patterns, which are different from each other. In addition, the temporary correction value may be calculated by performing conversion processing, in which matrix processing and a one-dimensional look-up table (1D-LUT) are combined, on the Bp image signal, the Bq image signal, the Gr image signal, and the Rs image signal.

Figure 11:
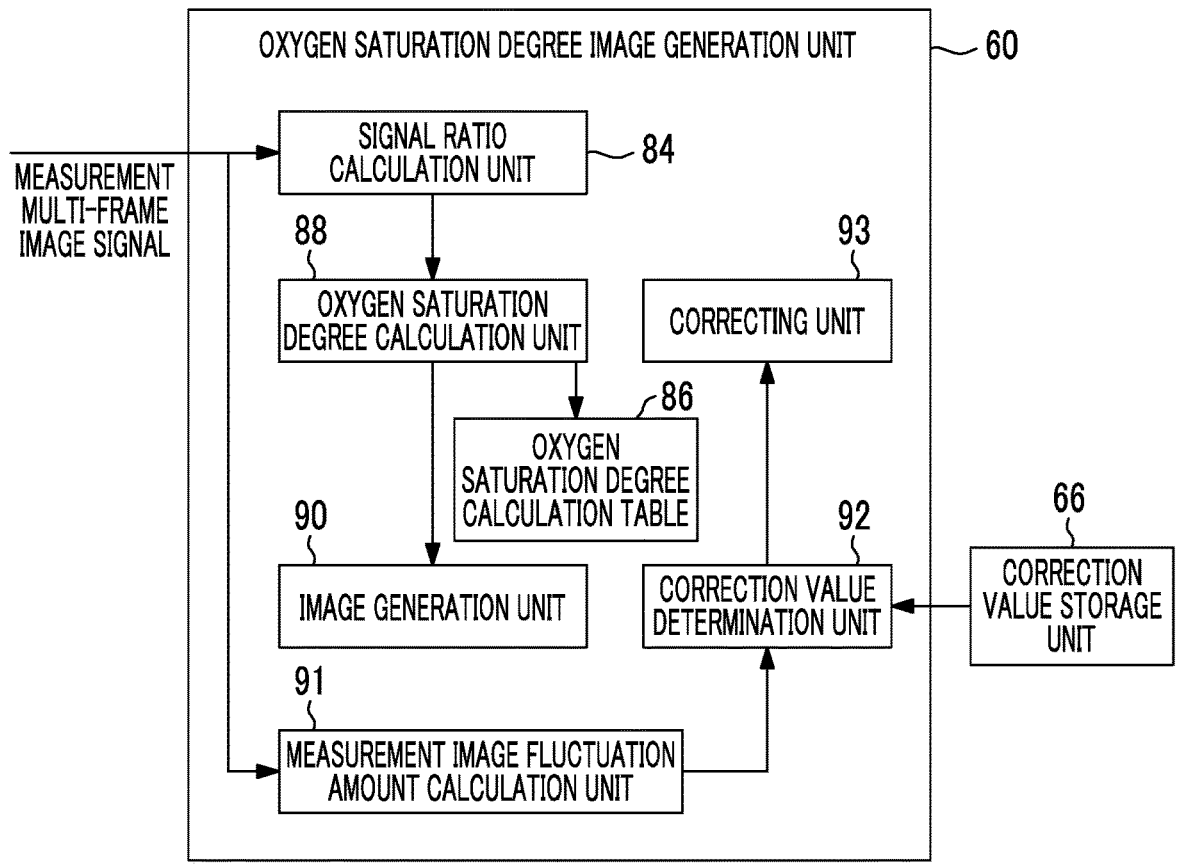
FIG. 11 is a block diagram illustrating the functions of an oxygen saturation degree image generation unit.

As illustrated in FIG. 11, the oxygen saturation degree image generation unit 60 includes a signal ratio calculation unit 84, an oxygen saturation degree calculation table 86, an oxygen saturation degree calculation unit 88, an image generation unit 90, a measurement image fluctuation amount calculation unit 91, a correction value determination unit 92, and a correcting unit 93. The signal ratio calculation unit 84 calculates the signal ratios to be used for the calculation of the oxygen saturation degree by the oxygen saturation degree calculation unit 88, on the basis of the B1 image signal, the G2 image signal, and the R2 image signal that are the measurement multi-frame image signals. Specifically, the signal ratio calculation unit 84 calculates a signal ratio B1/G2 of the B1 image signal and the G2 image signal, a signal ratio R2/G2 of the R2 image signal and the G2 image signal, and a signal ratio G2/B2 of the G2 image signal and the B2 image signal, respectively, for each pixel.

Figure 12:
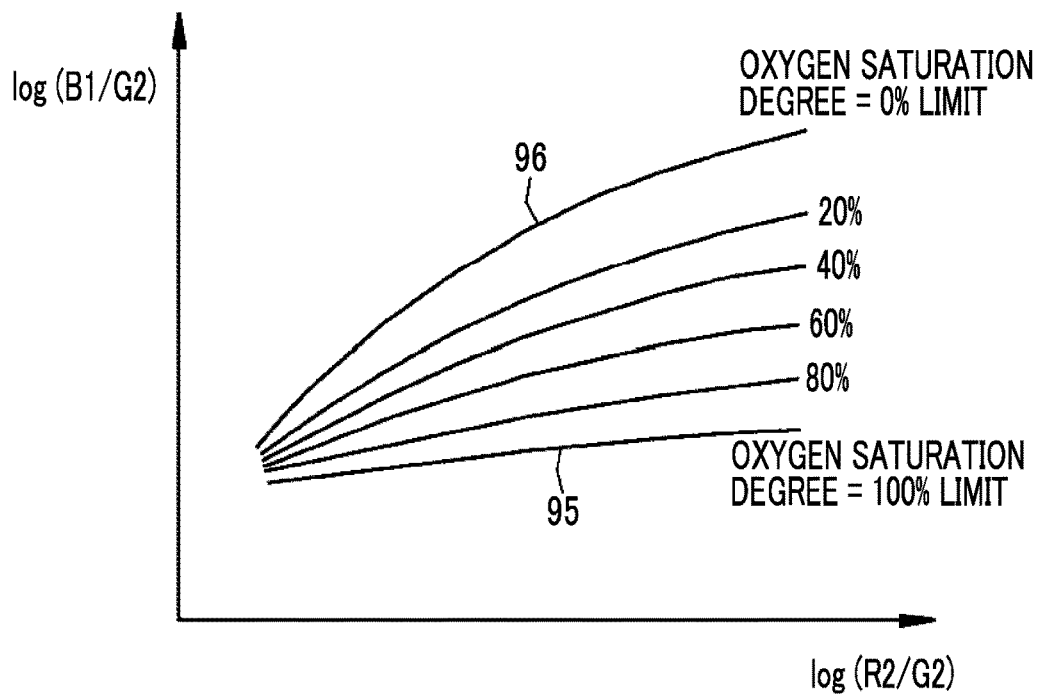
FIG. 12 is a graph illustrating the positions of contour lines of oxygen saturation degree in a feature space N in which a vertical axis represents Log (B1/G2) and a horizontal axis represents Log (R2/G2).

The oxygen saturation degree calculation table 86 (corresponding to the "calculation table") stores a correlation between respective signal ratios calculated by the signal ratio calculation unit 84 and the oxygen saturation degree. In a case where the correlation is expressed on a feature space N formed by a vertical axis Log (B1/G2) and a horizontal axis Log (R2/G2), as illustrated in FIG. 12, contour lines obtained by connecting portions with same oxygen saturation degree together are formed substantially in a horizontal axis direction on the feature space N. Additionally, the contour lines are located closer to a lower side in a vertical axis direction as the oxygen saturation degree becomes larger. For example, a contour line 95 whose oxygen saturation degree is 100% is located below a contour line 96 whose oxygen saturation degree is 0%. The information on the above contour lines is created on the basis of the image signals obtained in the reference image state.

In addition, the positions and the shapes of the contour lines in the feature space N are obtained in advance by physical simulation of light scattering. Additionally, in the oxygen saturation degree calculation table 86, the correlations between the signal ratio B1/G2 and R2/G2 and the oxygen saturation degree are stored. However, the invention is not limited to the correlations with the signal ratio B1/G2 and R2/G2, and a correlation between a first calculated value obtained by performing specific calculation (for example, difference processing) based on the B1 image signal, the G2 image signal, and the R2 image signal, and the oxygen saturation degree may be stored.

Figure 13:
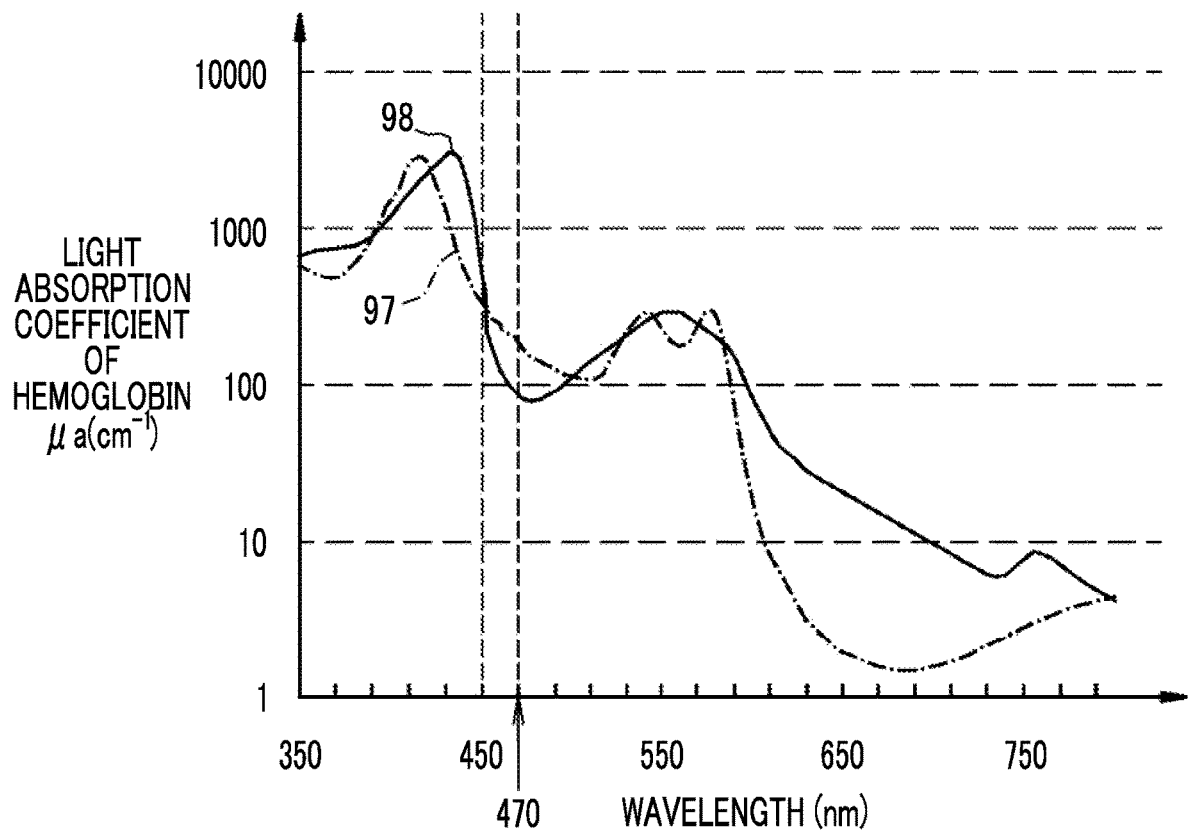
FIG. 13 is a graph illustrating the light absorption coefficients of an oxygenated hemoglobin and a reduced hemoglobin.

The above correlation is closely correlated with light-absorption characteristics and light-scattering characteristics of an oxygenated hemoglobin (graph 97) and a reduced hemoglobin (graph 98) that are illustrated in FIG. 13. For example, in a wavelength band with a large difference between the light absorption coefficients of the oxygenated hemoglobin and the reduced hemoglobin like the wavelength band 470±10 nm of the second blue light BL, light absorption amount varies depending on the oxygen saturation degree of hemoglobin. Therefore, it is easy to handle information on the oxygen saturation degree. Hence, it is possible to calculate the oxygen saturation degree by using the signal ratio B1/G2 including the B1 image signal corresponding to the second blue light BL with a center wavelength of 470 nm. However, the signal ratio B1/G2 has a high dependence on not only the oxygen saturation degree but the amount of blood. Thus, by using the signal ratio R2/G2 that vary mainly depending on the amount of blood in addition to the signal ratio B1/G2, it is possible to accurately obtain the oxygen saturation degree without being affected by the amount of blood. In addition, since the wavelength band of 540±20 nm of the green light included in the G2 image signal has a relatively high light absorption coefficient of hemoglobin, the wavelength band is a wavelength band where the light absorption amount easily varies depending on the amount of blood.

Figure 14:
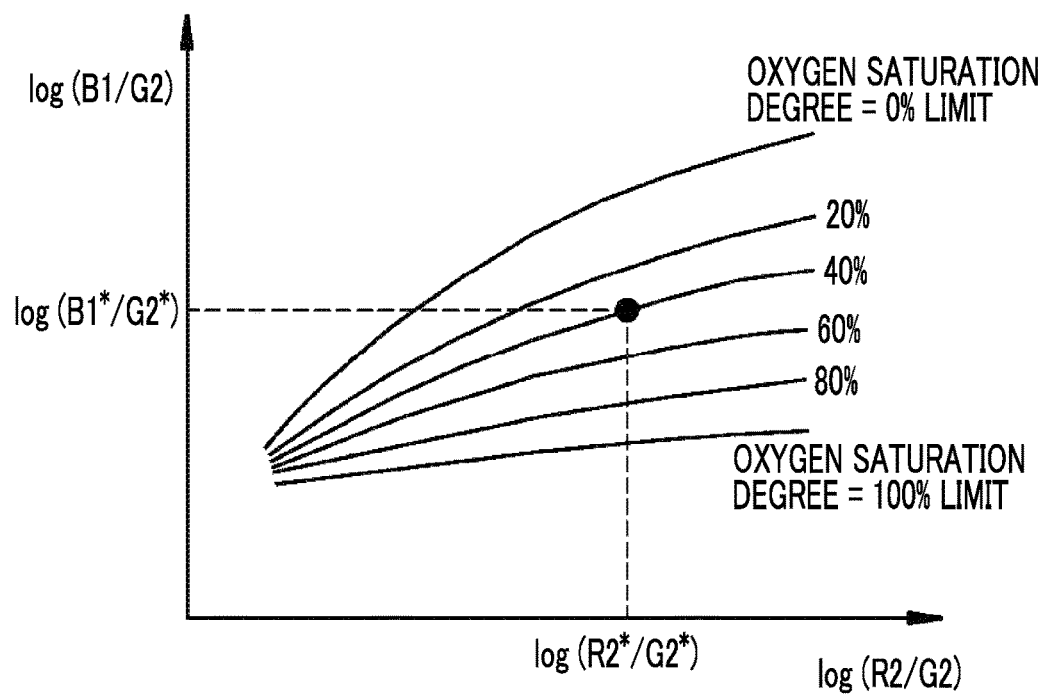
FIG. 14 is an explanatory view illustrating a method for calculating the oxygen saturation degree.

The oxygen saturation degree calculation unit 88 refers to a correlation stored in the oxygen saturation degree calculation table 86, and calculates an oxygen saturation degree corresponding to the signal ratios B1/G2 and R2/G2 for each pixel. For example, as illustrated in FIG. 14, in a case where the correlation stored in the oxygen saturation degree calculation table 86 is referred to, an oxygen saturation degree corresponding to the signal ratios B1*/G2* and R2*/G2* of a specific pixel is "40%". Hence, the oxygen saturation degree calculation unit 88 calculates the oxygen saturation degree as "40%".

In addition, the signal ratio B1/G2, R2/G2 hardly become extremely large or extremely small. That is, the combination of the respective values of the signal ratios B1/G2 and R2/G2 is hardly distributed below the contour line 95 (refer to FIG. 13) of an upper limit that is an oxygen saturation degree of 100% or conversely, the combination is hardly distributed above the contour line 96 (refer to FIG. 13) of a lower limit that is an oxygen saturation degree of 0%. However, in a case where the combination is distributed below the contour line 95 of the upper limit, the oxygen saturation degree is 100%, and in a case where the combination is distributed above the contour line 96 of the lower limit, the oxygen saturation degree calculation unit 88 sets the oxygen saturation degree as 0%. Additionally, in a case where a point corresponding to the signal ratios B1/G2 and R2/G2 is not distributed between the contour line 95 of the upper limit and the contour line 96 of the lower limit, a display may be performed such that it can be seen that the reliability of the oxygen saturation degree in the pixel is low, and the oxygen saturation degree may not be calculated.

The image generation unit 90 creates an oxygen saturation degree image obtained by imaging the oxygen saturation degree, using the oxygen saturation degree calculated by the oxygen saturation degree calculation unit 88. Specifically, the image generation unit 90 acquires the B2 image signal, the G2 image signal, and the R2 image signal, and specifies a gain according to the oxygen saturation degree to these image signals for each pixel. Then, RGB image data is created using the B2 image signal, the G2 image signal, and the R2 image signal to which the gain is specified. For example, the image generation unit 90 multiplies all the B2 image signal, the G2 image signal, and the R2 image signal by the same gain "1" in pixels with an oxygen saturation degree of 60% or more. In contrast, in pixels with an oxygen saturation degree of less than 60%, the B2 image signal is multiplied by a gain of less than "1", and the G2 image signal and the R2 image signal are multiplied by a gain of "1" or more. RGB image data created using the B2 image signal, the G2 image signal, and the R2 image signal after this gain processing is the oxygen saturation degree image.

In the oxygen saturation degree image generated by the image generation unit 90, a high-oxygen region (a region where the oxygen saturation degree is 60% to 100%) is expressed in the same color as a normal observation image. On the other hand, a low-oxygen region where the oxygen saturation degree is less than a specific value (a region where the oxygen saturation degree is 0% to 60%) is expressed in a color (pseudo-color) different from the normal observation image.

In addition, in the present embodiment, the image generation unit 90 multiplies the low-oxygen region to a gain for pseudo-coloring. However, the gain according to the oxygen saturation degree may also be given to the high-oxygen region, and the overall oxygen saturation degree image may be pseudo-colored. Additionally, although the low-oxygen region and the high-oxygen region are divided at an oxygen saturation degree of 60%, this boundary is also optional.

The measurement image fluctuation amount calculation unit 91 calculates a measurement image fluctuation amount from the B1 image signal, the G2 image signal, and the R2 image signal that are the measurement multi-frame image signals. The measurement image fluctuation amount shows how much an image state based on the measurement multi-frame image signals fluctuates from the reference image state due to the various fluctuation factors, such as the positional shift between frames, similar to the correction image fluctuation amount. In the measurement image fluctuation amount calculation unit 91, calculation of the measurement image fluctuation amount is performed regarding all types of correction image fluctuation amounts calculated by the correction image fluctuation amount calculation unit 70. For example, in a case where the fluctuation amount of the yellow coloring agent and the positional shift between frames are calculated as the correction image fluctuation amount, the fluctuation amount of the yellow coloring agent and the positional shift between frames are similarly calculated as the measurement image fluctuation amount. The measurement image fluctuation amount calculated by the measurement image fluctuation amount calculation unit 91 is transmitted to the correction value determination unit 92.

In addition, a method for calculating the measurement image fluctuation amount is the same as the method for calculating the correction image fluctuation amount. Additionally, similar to the case where the correction image fluctuation amount is calculated, in the measurement multi-frame image signals, the measurement image fluctuation amount may be calculated in all pixel regions, or some pixel regions may be set as a measurement image fluctuation amount calculation region and the measurement image fluctuation amount may be calculated within the set measurement image fluctuation amount calculation region. The measurement image fluctuation amount calculation region is set by the same method as the correction image fluctuation amount calculation region.

The correction value determination unit 92 compares the input measurement image fluctuation amount with the correction image fluctuation amount stored in the correction value storage unit 66. Also, the correction value determination unit 92 determines the temporary correction value associated with the correction image fluctuation amount nearest to the measurement image fluctuation amount as the measurement correction value, as a result of comparing both the fluctuation amounts. In the correction value determination unit 92, all types of correction image fluctuation amounts stored in the correction value storage unit 66 are compared with the measurement image fluctuation amount, and determination of the measurement correction value is performed. In addition, in a case where the correction image fluctuation amount calculation region and the measurement image fluctuation amount calculation region are set, it is preferable to compare the correction image fluctuation amount and the measurement image fluctuation amount in a region where the correction image fluctuation amount calculation region and the measurement image fluctuation amount calculation region overlap each other.

For example, in a case where the fluctuation amount and the temporary correction value as illustrated in FIG. 15 are stored in the correction value storage unit 66, a method for determining the measurement correction value is as follows. In addition, a fluctuation amount X1 of the yellow coloring agent obtained from a correction multi-frame image signal at the first timing T1 and a temporary correction value AX1 for the yellow coloring agent, and a positional shift amount Y1 between frames and a temporary correction value AY1 for the positional shift between frames are stored in the correction value storage unit 66. Additionally, a fluctuation amount X2 of the yellow coloring agent obtained from a correction multi-frame image signal at the second timing T2 and a temporary correction value AX2 for the yellow coloring agent, and a positional shift amount Y2 between frames and a temporary correction value AY2 for the positional shift between frames are stored in the correction value storage unit 66. For example, in a case where the fluctuation amount X1 of the yellow coloring agent is input as the measurement image fluctuation amount, the temporary correction value AX1 for the yellow coloring agent at the first timing T1 is determined as the measurement correction value for the yellow coloring agent. Additionally, in a case where the positional shift amount Y2 between frames is input as the measurement image fluctuation amount, the temporary correction value AY2 for the positional shift between frames at the second timing T2 is determined as the measurement correction value for the positional shift between frames.

The correcting unit 93 corrects the contents of the oxygen saturation degree calculation processing in the oxygen saturation degree calculation unit 88 on the basis of the measurement correction value determined by the correction value determination unit 92. In the correcting unit 93, correction of the oxygen saturation degree calculation table 86, correction of the signal ratios B1/G2 and R2/G2 to be used by the oxygen saturation degree calculation unit 88, or correction of the oxygen saturation degree calculated by the oxygen saturation degree calculation unit 88 is performed as the correction of the contents of the oxygen saturation degree calculation processing. Regarding the correction of the oxygen saturation degree calculation table 86, the correcting unit 93 performs the correction of moving all the contour lines by a measurement correction value for table correction in the direction of a vertical axis Log (B1/G2) or in the direction of a horizontal axis Log (R2/G2) in the feature space N.

For example, in a case where the difference ΔZ serving as the correction image fluctuation amount illustrated in FIG. 10 is used as the fluctuation amount of the yellow coloring agent, as illustrated in FIG. 16, the correction of moving all the contour lines 99 in the direction of the vertical axis Log (B1/G2) by the measurement correction value for the yellow coloring agent is performed. Accordingly, the correlation of the oxygen saturation degree calculation table 86 is updated. By calculating the oxygen saturation degree using the oxygen saturation degree calculation table 86 after this correlation updating, the oxygen saturation degree can be accurately calculated even in a situation in which various fluctuation factors, such as the influence of the yellow coloring agent on the observation target and the positional shift between frames, occur in addition to a case where various parts or patients are different.

Regarding the correction of the signal ratios B1/G2 and R2/G2 to be used by the oxygen saturation degree calculation unit 88, before the oxygen saturation degree calculation table 86 is referred to in the oxygen saturation degree calculation unit 88, the correcting unit 93 adds the measurement correction value for the signal ratios to at least one of the input signal ratios B1/G2 or R2/G2. Also, the oxygen saturation degree calculation unit 88 calculates the oxygen saturation degree corresponding to the signal ratios B1/G2 and R2/G2, to which the measurement correction value for the signal ratios is added, from the oxygen saturation degree calculation table 86.

Regarding the correction of the oxygen saturation degree calculated by the oxygen saturation degree calculation unit 88, first, a temporary oxygen saturation degree is calculated on the basis of the oxygen saturation degree calculation table 86 in the oxygen saturation degree calculation unit 88. Then, the correcting unit 93 adds the measurement correction value for the oxygen saturation degree to the temporary oxygen saturation degree. The oxygen saturation degree calculation unit 88 calculates the oxygen saturation degree, to which the measurement correction value for the oxygen saturation degree is added, as a formal oxygen saturation degree.

Figure 17:
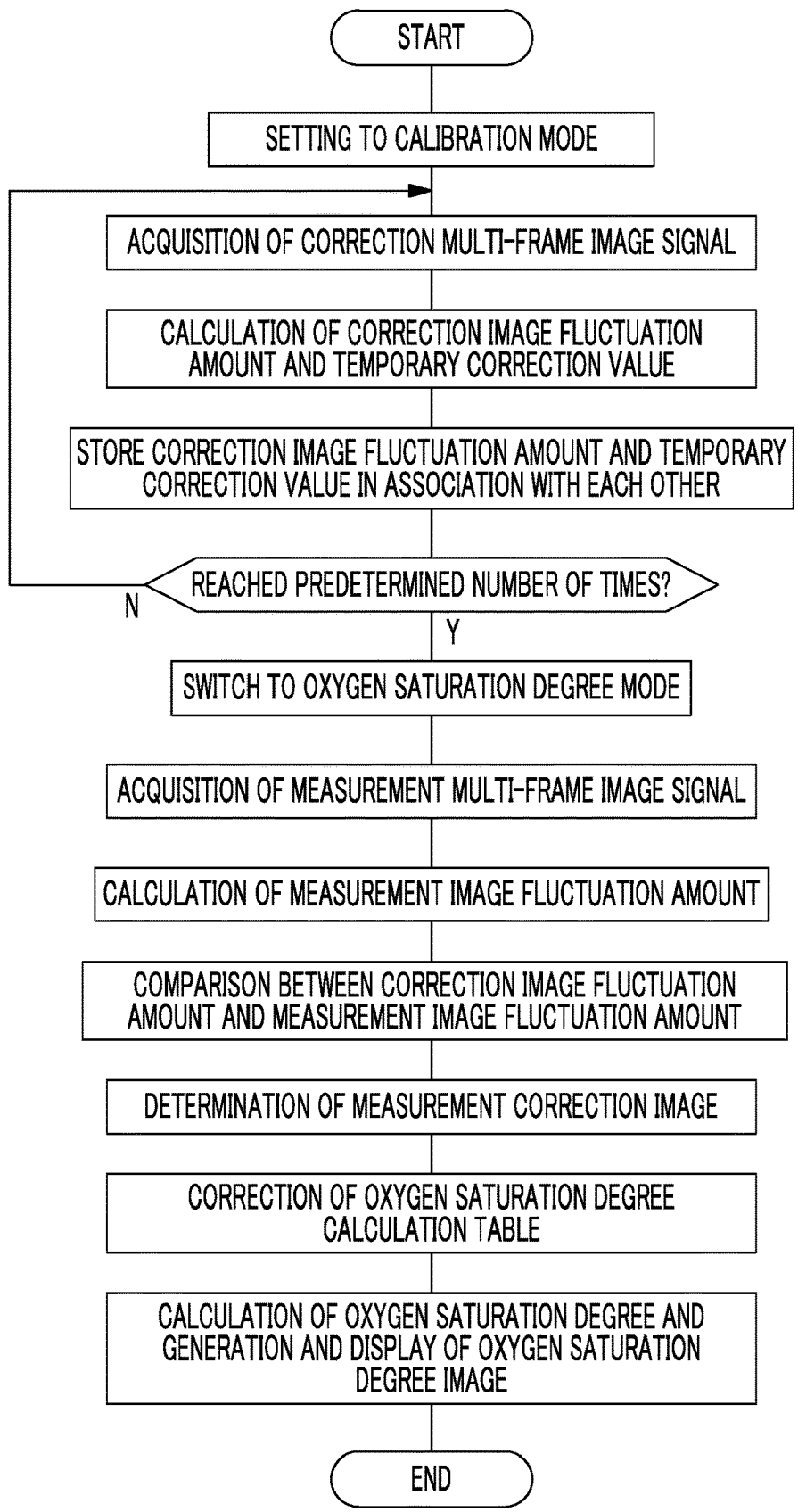
FIG. 17 is a flowchart illustrating a series of flow in the first embodiment.

Next, a series of flow will be described along a flowchart of FIG. 17. A mode switchover SW 12ƒ is operated to set the calibration mode. Accordingly, the first blue light BS, the second blue light BL, the green light G, and the red light R are sequentially emitted in by sequentially switching on the respective LEDs 20a to 20d. The four-color lights are radiated to the observation target, and are imaged by the imaging sensor 44. Accordingly, in the calibration mode, correction multi-frame image signals including the Bp image signal, the Bq image signal, the Gr image signal, and the Rs image signal are obtained. In addition, in a case where the calibration mode is set and in a case where there is a concern about contamination caused by the yellow coloring agent or the like on the observation target, the user can remove most of the influence of the yellow coloring agent or the like in advance by jetting the cleaning liquid from the distal end part 12*d* of the endoscope 12 to the observation target. This cleaning may be performed in a case where there is a concern about the contamination caused by the yellow coloring agent or the like, or may not be performed as long as the cleaning is reliably performed in advance.

Next, the correction image fluctuation amount calculation unit 70 calculates the correction image fluctuation amount on the basis of the correction multi-frame image signals. After the correction image fluctuation amount is calculated, the correction value calculation unit 72 calculates the temporary correction value on the basis of the correction image fluctuation amount. The associating unit 76 associates the correction image fluctuation amount with the temporary correction value calculated on the basis of this correction image fluctuation amount, and stores the associated correction image fluctuation amount and temporary correction value in the correction value storage unit 66. Then, the acquisition of the correction multi-frame image signals, the calculation of the correction image fluctuation amount and its temporary correction value, and the series of calibration processing of storage to the correction value storage unit 66 described above are repeatedly performed by a predetermined number of times.

In a case where the number of times of processing of the calibration processing reaches the predetermined number of times, automatic switching from the calibration mode to the oxygen saturation degree mode is performed. In the oxygen saturation degree mode, the observation target is alternately irradiated with the second blue light BL the first blue light BS, the green light G, and the red light R, and is imaged by the imaging sensor 44. Accordingly, the measurement multi-frame image signals including the B1 image signal, the G2 image signal, and the R2 image signal, which are required for the calculation of the oxygen saturation degree, are obtained.

After the measurement multi-frame image signals are acquired, the measurement image fluctuation amount calculation unit 91 calculates the measurement image fluctuation amount on the basis of the measurement multi-frame image signals. After the measurement image fluctuation amount is calculated, the correction value determination unit 92 compares the measurement image fluctuation amount, and the correction image fluctuation amount stored in the correction value storage unit 66. As a result of the comparison, the temporary correction value associated with the correction image fluctuation amount nearest to the measurement image fluctuation amount is determined as the measurement correction value. The correction of the oxygen saturation degree calculation table 86 is performed on the basis of this measurement correction value.

Next, the signal ratio B1/G2 of the B1 image signal and the G2 image signal and the signal ratio R2/G2 of the R2 image signal and the G2 image signal are calculated. Then, the oxygen saturation degree calculation unit 88 calculates the oxygen saturation degree with reference to the correlation stored in the corrected oxygen saturation degree calculation table 86 on the basis of the calculated signal ratios B1/G2, R2/G2. The oxygen saturation degree image is generated on the basis of the calculated oxygen saturation degree, and is displayed on the monitor 18. In addition, although the correction of the oxygen saturation degree calculation table 86 is performed before the calculation of the oxygen saturation degree, the correction of the signal ratios B1/G2 and R2/G2 may be performed. Alternatively, the correction of the temporary oxygen saturation degree may be performed after the temporary oxygen saturation degree is calculated.

Figure 18:
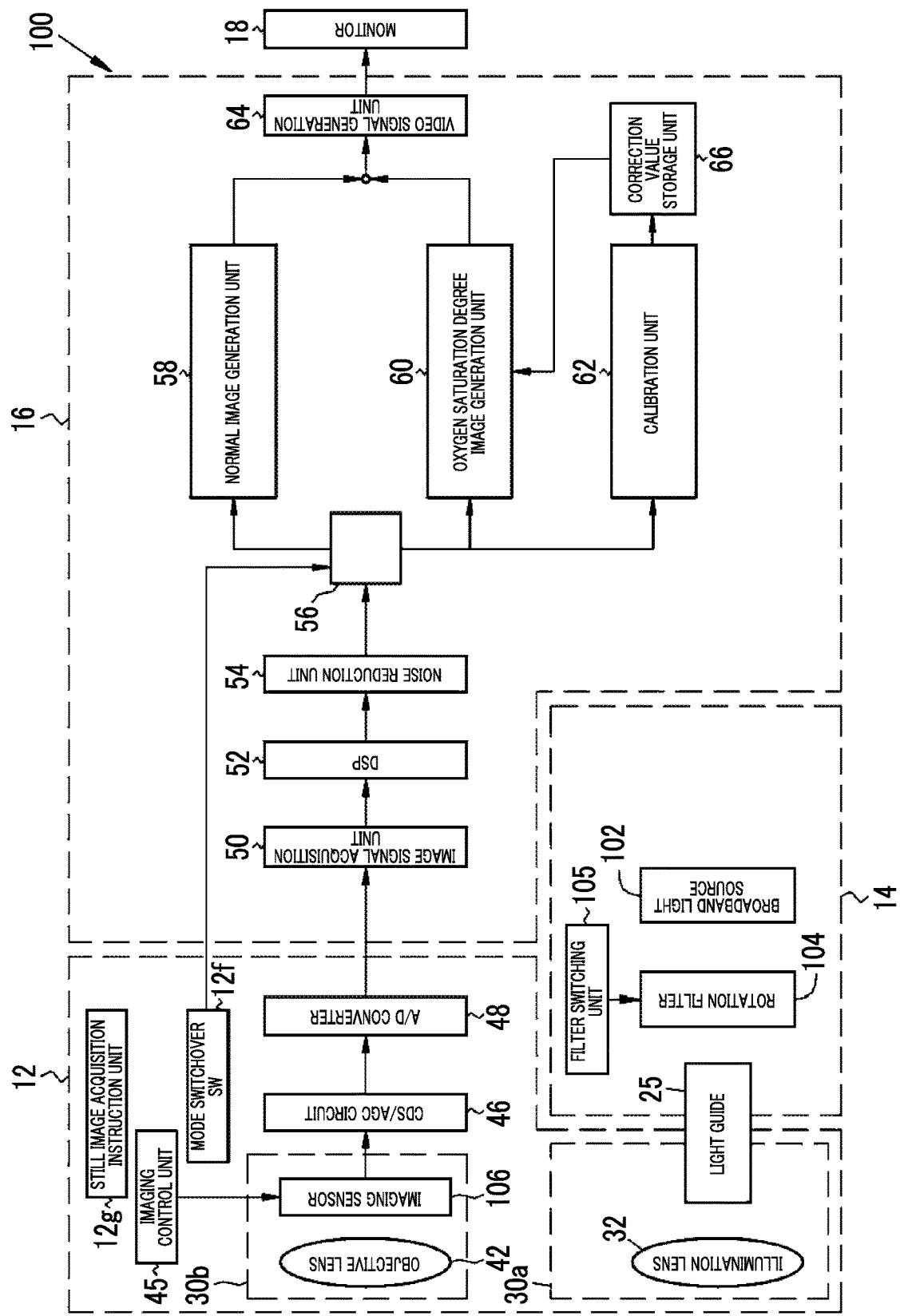
FIG. 18 is a block diagram illustrating the functions of a rotation filter type endoscope system.

In addition, illumination of the observation target may be performed using a broadband light source, such as a xenon lamp, and a rotation filter instead of the four-color LEDs 20*a* to 20*d* illustrated in the first embodiment above. As illustrated in FIG. 18, in an endoscope system 100, in the light source device 14, a broadband light source 102, a rotation filter 104, and a filter switching unit 105 are provided instead of the four-color LEDs 20*a* to 20*d*. Additionally, the imaging optical system 30*b* is provided with a monochrome imaging sensor 106 that is not provided with a color filter instead of the color imaging sensor 44.

The broadband light source 102 is a xenon lamp, a white LED, or the like, and emits white light whose wavelength band ranges from blue to red. The rotation filter 104 includes an inner filter 108 provided inside and an outer filter 109 provided outside (refer to FIG. 19). The filter switching unit 105 moves the rotation filter 104 in a radial direction, inserts the inner filter 108 of the rotation filter 104 into an optical path for the white light in a case where the normal mode is set by the mode switchover SW 12*f*, and inserts the outer filter 109 of the rotation filter 104 into the optical path for the white light in a case where the oxygen saturation degree mode or the calibration mode is set.

Figure 19:
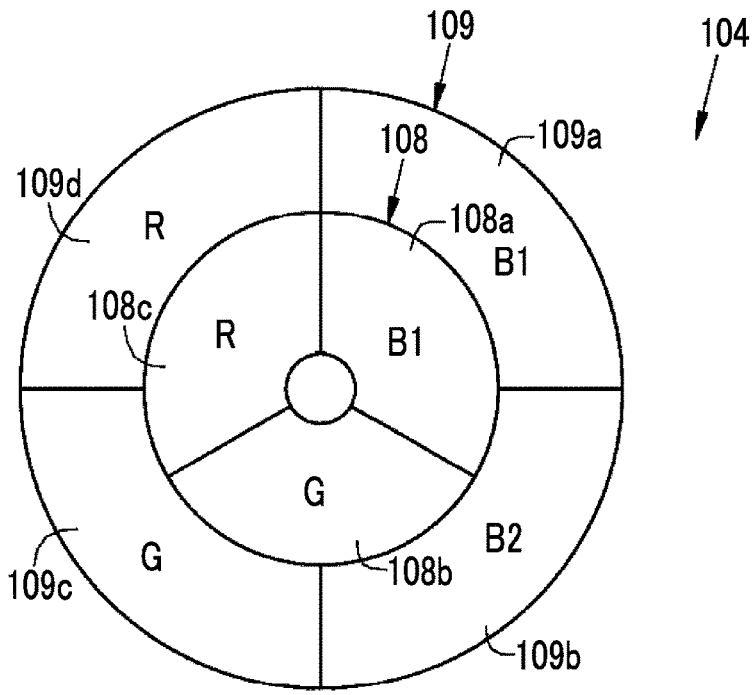
FIG. 19 is a plan view of a rotation filter.

As illustrated in FIG. 19, a B1 filter 108*a* that allows the first blue light BS of the white light to be transmitted therethrough, a G filter 108*b* that allows the green light G of the white light to be transmitted therethrough, and an R filter 108*c* that allows the red light R of the white light to be transmitted therethrough are provided in a circumferential direction at the inner filter 108. Hence, in the normal mode, the first blue light BS, the green light G, and the red light R are alternately radiated to the observation target by the rotation of the rotation filter 104.

A B1 filter 109*a* that allows the first blue light BS of the white light to be transmitted therethrough, a B2 filter 109*b* that allows the second blue light BL of the white light to be transmitted therethrough, a G filter 109*c* that allows the green light G of the white light to be transmitted therethrough, and an R filter 109*d* that allows the red light R of the white light to be transmitted therethrough are provided in the circumferential direction at the outer filter 109. Hence, in the oxygen saturation degree mode or the calibration mode, the first blue light BS, the second blue light BL, the green light G, and the red light R are alternately radiated to the observation target as the rotation filter 104 rotates.

In the endoscope system 100, in the normal mode, whenever the observation target is illuminated by the first blue light BS, the green light G, and the red light R, the observation target is imaged by the monochrome imaging sensor 106. Accordingly, the Bc image signal, the Gc image signal, and the Rc image signal are obtained. Then, a normal image is created by the same method as the first embodiment above on the basis of the three-color image signals.

On the other hand, in the oxygen saturation degree mode, whenever the observation target is illuminated by the first blue light BS, the second blue light BL, the green light G, and the red light R, the observation target is imaged by the monochrome imaging sensor 106. Accordingly, measurement multi-frame image signals including the B2 image signal, the B1 image signal and the G2 image signal, and the R2 image signal are obtained. On the basis of this measurement multi-frame image signals, the generation of the oxygen saturation degree image is performed by the same method as above. Additionally, in the calibration mode, correction multi-frame image signals including the Bp image signal, the Bq image signal, the Gr image signal, and the Rs image signal are obtained. On the basis of the four-color image signals, the calculation of the temporary correction value is performed by the same method as above.

In addition, in the above embodiment, the first blue light BS whose wavelength band is 450±10 nm is used in order to correct the correlation in the calibration mode. However, the light absorption coefficients of the oxygenated hemoglobin and the reduced hemoglobin may be in the same wavelength band, and light in a wavelength band where the light absorption coefficient of the yellow coloring agent is larger compared to the other wavelength bands may be used. For example, green narrow-band light whose wavelength band is 500±10 nm may be used instead of the first blue light BS.

In addition, in the above embodiment, the oxygen saturation degree serving as the functional living body characteristic amount has been described as an example. However, the invention can also be applied to a morphologic living body characteristic amount other than the functional living body characteristic amount. The morphologic living body characteristic amount is, for example, the number of pieces, the number of branches, a branch angle, a distance between branch points, the number of intersections, thickness, a change in thickness, the degree of complexity of a change in thickness, length, intervals, depth with a mucous membrane as a reference, a height difference, inclination, area, density, contrast, color, a change in color, the degree of meandering, blood concentration, an artery fraction, a vein fraction, the concentration of an administered coloring agent, a traveling pattern, or a blood flow rate, in terms of the blood vessels.

For example, in a case where the blood vessel density is calculated as the morphologic living body characteristic amount, it is preferable to perform the calculation as follows. First, the calibration mode is set, the observation target is alternately radiated with first shortwave light SL1 having a center wavelength of 405 nm and second shortwave light SL2 having a center wavelength of 445 nm, and imaging of the observation target is performed by the imaging sensor 44 for each irradiation. Accordingly, the correction multi-frame image signals including a Bx image signal corresponding to the first shortwave light SL1 and a By image signal corresponding to the second shortwave light SL2 are obtained. At least one set of the correction multi-frame image signals are acquired similarly to the above.

Then, the correction image fluctuation amount and its temporary correction value are calculated using the correction multi-frame image signals by the same calibration unit 62, and the calculated the correction image fluctuation amount and its temporary correction value are associated with each other and stored in the correction value storage unit 66. In addition, the correction image fluctuation amount includes, for example, a positional shift amount between the Bx image signal and the By image signal.

Figure 20:
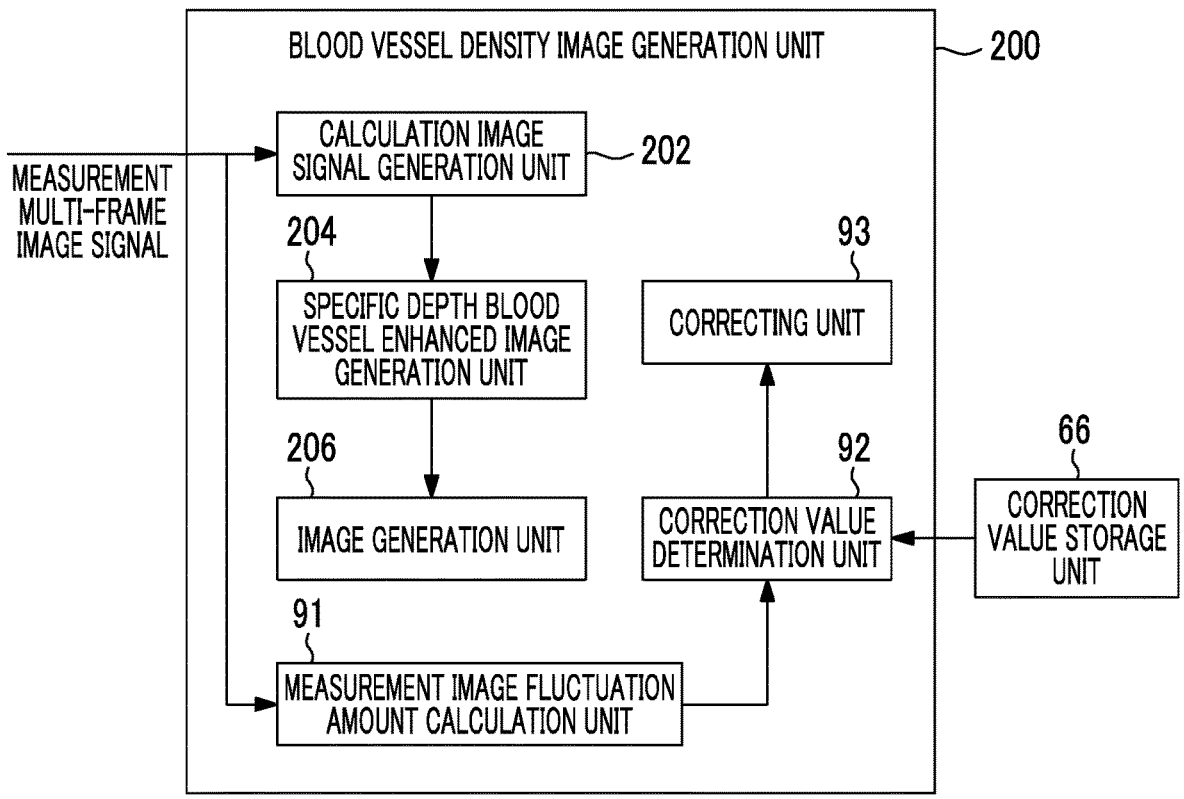
FIG. 20 is a block diagram illustrating the functions of a blood vessel density image generation unit.

Next, in the blood vessel density mode (corresponding to the "measurement mode") performed in the calibration mode, the observation target is alternately irradiated with the first shortwave light SL1 and the second shortwave light SL2 and is imaged by the imaging sensor 44. Accordingly, the measurement multi-frame image signals including the Bx image signal corresponding to the first shortwave light SL1 and the By image signal corresponding to the second shortwave light SL2 are obtained. On the basis of the measurement multi-frame image signals, a blood vessel density image is generated by the blood vessel density image generation unit 200 illustrated in FIG. 20.

The blood vessel density image generation unit 200 includes a calculation image signal generation unit 202, a specific depth blood vessel enhanced image generation unit 204, or an image generation unit 206, and includes the same measurement image fluctuation amount calculation unit 91, the correction value determination unit 92, or the correcting unit 93 as the above embodiment. The calculation image signal generation unit 202 performs calculation for each pixel using the Bx image signal and the By image signal, and generates a calculation image signal. It is preferable that the calculation is difference processing or ratio calculation. In a case where the difference processing is performed, after the Bx image signal and the By image signal are log-transformed, the difference processing of the Bx image signal and the By image signal is performed after the logarithmic transformation. Additionally, in the ratio calculation, the Bx image signal and the By image signal are not log-transformed but the Bx image signal is divided by the By image signal or the By image signal is divided by the Bx image signal.

The specific depth blood vessel enhanced image generation unit 204 allocates either the Bx image signal or the By image signal to t a luminance channel Y, and generates a specific depth blood vessel enhanced image, in which a blood vessel traveling pattern at a specific depth is enhanced in colors, by allocating the calculation image signal to two color difference channels Cb and Cr. The generated specific depth blood vessel enhanced image is displayed on the monitor 18 together with the blood vessel density image to be described below. In addition, in a case where the calculation image signal is allocated to the color difference channels Cb and Cr, it is preferable to allocate a value obtained by multiplying the calculation image signal by a color coefficient p to the color difference channel Cb and to allocate a value obtained by multiplying the calculation image signal by a color coefficient q (different from the color coefficient p) to the color difference channel Cr. The reason why the color coefficients p and q are used in this way is to adjust the tint of blood vessels and the color of other observation targets.

The image generation unit 206 generates the blood vessel density image by calculating the blood vessel density for each predetermined region in the specific depth blood vessel enhanced image and allocating a color in accordance with the calculated blood vessel density. In the blood vessel density image, it is preferable to perform color setting in which a difference becomes clear in a high-density region where the blood vessel density is high and a low-density region where the blood vessel density is low. In a case where the blood vessel density is calculated as described above, the correcting unit 93 corrects the contents of calculation processing of the blood vessel density on the basis of the measurement correction value. The correction of the contents of the calculation processing of the blood vessel density by the correcting unit 93 is performed at least either before the calculation the blood vessel density or after the calculation of the blood vessel density. For example, in the case of after the calculation of the blood vessel density, it is preferable that the correcting unit 93 performs the correction of adding a measurement correction value for blood vessel density to the calculated blood vessel density.

Second Embodiment

In the first embodiment, the correction image fluctuation amount and the measurement image fluctuation amount are directly compared with each other and the correction image fluctuation amount nearest to the measurement image fluctuation amount is selected. However, in the second embodiment, a difference between the correction image fluctuation amount and the measurement image fluctuation amount is quantified, and selection of the correction image fluctuation amount is performed on the basis of the quantified value. The others are the same as those of the first embodiment.

Figure 21:
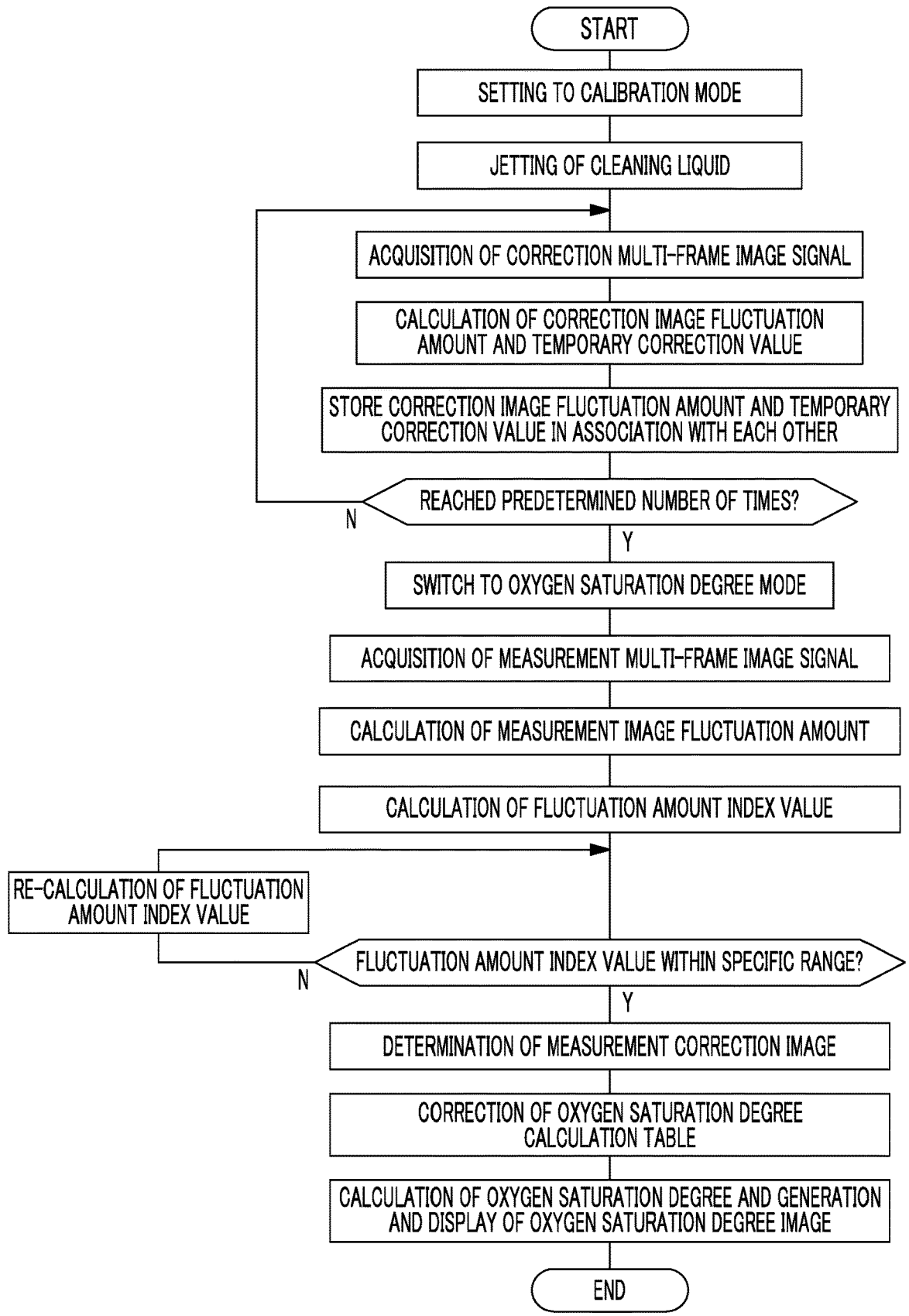
FIG. 21 is a flowchart illustrating a series of flow in a second embodiment.

In the second embodiment, in the correction value determination unit 92 within the oxygen saturation degree image generation unit 60, in a case where the correction image fluctuation amount and the measurement image fluctuation amount are compared with each other, calculation of a difference or a ratio between the correction image fluctuation amount and the measurement image fluctuation amount is performed, a fluctuation amount index value obtained by quantifying the difference between both the fluctuation amounts is calculated. Also, as illustrated in FIG. 21, in a case where the fluctuation amount index value falls within a specific range, the correction value determination unit 92 determines the temporary correction value associated with the correction image fluctuation amount at that time as the measurement correction value. After the determination of the measurement correction value, correction is performed by the correcting unit 93 as in the first embodiment. In addition, in a case where a plurality of the fluctuation amount index values within the specific range are present and a plurality of the temporary correction values are determined as measurement correction values, it is preferable to use a representative value of the plurality of temporary correction values as a formal measurement correction value. As the representative value, it is preferable to set an average value or a median value of the plurality of temporary correction values.

Here, in a case where the fluctuation amount index value is the difference between the correction image fluctuation amount and the measurement image fluctuation amount, it is preferable that the "specific range" is a certain range (for example, a range from "dx" smaller than "0" to "dy" larger than "0") including "0". Additionally, in a case where the fluctuation amount index value is the ratio between the correction image fluctuation amount and the measurement image fluctuation amount, it is preferable that the "specific range" is a certain range (for example, a range from "cx" smaller than "1" to "cy" larger than "1") including "1".

Figure 22:
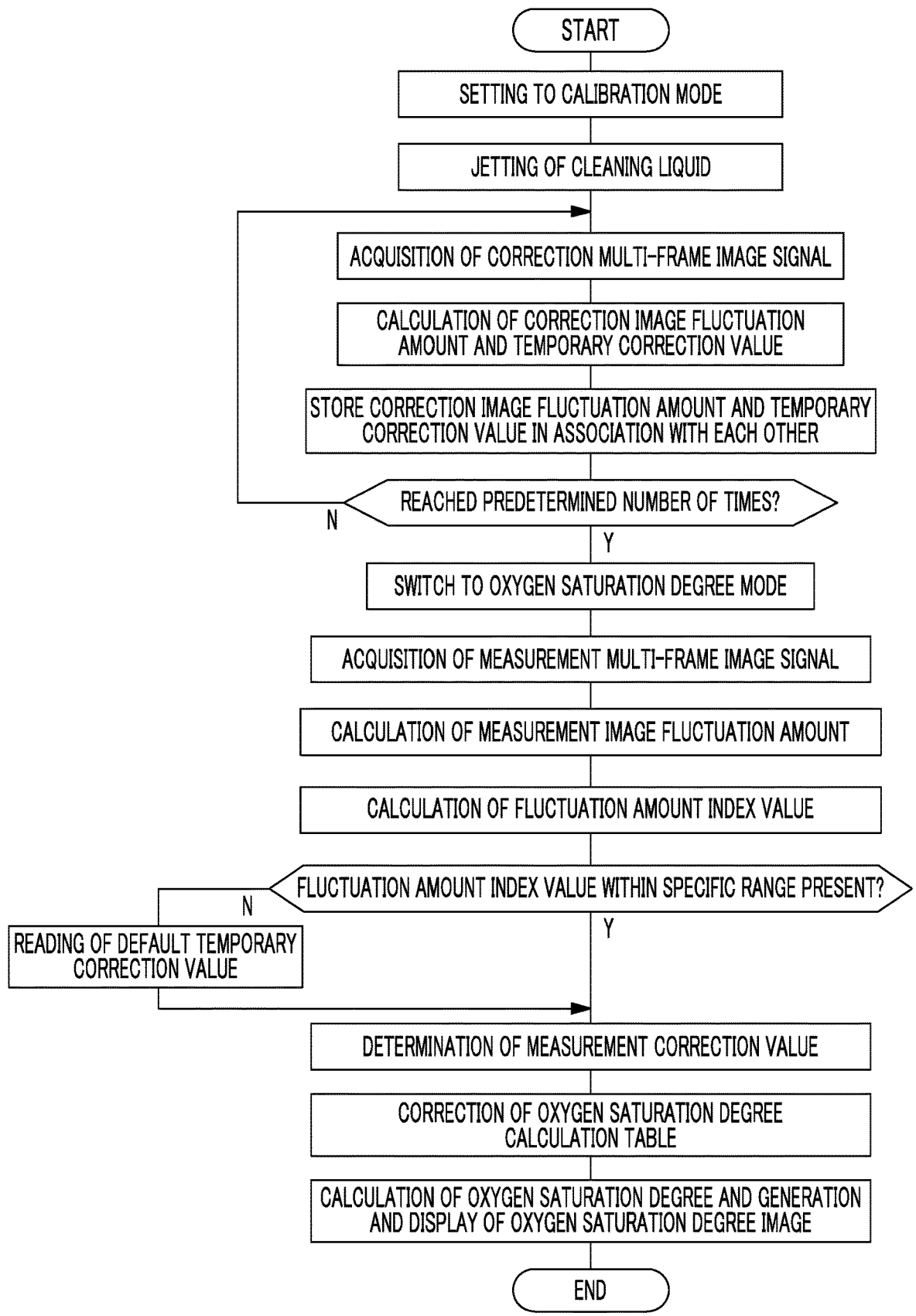
FIG. 22 is a flowchart illustrating a series of flow different from FIG. 21, in the second embodiment.

Meanwhile, in a case where the fluctuation amount index value does not fall within the specific range, the fluctuation amount index value is re-calculated instead of other correction image fluctuation amounts, and whether or not the fluctuation amount index value is determined not to fall within the specific range is determined. This determination is repeatedly performed until the fluctuation amount index value falls within the specific range. In addition, in a case where the fluctuation amount index value over the measurement image fluctuation amount falls within the specific range regarding all the correction image fluctuation amounts stored in the correction value storage unit 66, as illustrated in FIG. 22, the correction value determination unit 92 reads a predetermined default temporary correction value from the correction value storage unit 66. Then, the correction value determination unit 92 determines the read default temporary correction value as the measurement correction value.

EXPLANATION OF REFERENCES

- 10: endoscope system
- 12: endoscope
- 12*a*: insertion part
- 12*b*: operating part
- 12*c*: bending part
- 12*d*: distal end part
- 12*e*: angle knob
- 12*f*: mode switchover SW
- 12*g*: still image acquisition instruction unit
- 14: light source device
- 16: processor device
- 18: monitor
- 19: console
- 20: light source
- 20*a*: BS-LED
- 20*b*: BL-LED
- 20*c*: G-LED
- 20*d*: R-LED
- 21: light source control unit
- 23: optical-path coupling unit
- 25: light guide
- 30*a*: illumination optical system
- 30*b*: imaging optical system
- 32: illumination lens
- 42: objective lens
- 44: imaging sensor
- 45: imaging control unit
- 46: CDS/AGC circuit
- 48: A/D converter
- 50: image signal acquisition unit
- 52: DSP
- 54: noise reduction unit
- 56: image processing switching unit
- 58: normal image generation unit
- 60: oxygen saturation degree image generation unit
- 62: calibration unit
- 64: video signal generation unit
- 66: correction value storage unit
- 70: correction image fluctuation amount calculation unit
- 72: correction value calculation unit
- 76: associating unit
- 84: signal ratio calculation unit
- 86: oxygen saturation degree calculation table
- 90: image generation unit
- 91: measurement image fluctuation amount calculation unit
- 92: correction value determination unit
- 93: correcting unit
- 95: contour line
- 96: contour line
- 97: graph
- 98: graph
- 99: all contour lines
- 100: endoscope system
- 102: broadband light source
- 104: rotation filter
- 105: filter switching unit
- 106: imaging sensor
- 108: inner filter
- 108*a*: B1 filter
- 108*b*: G filter
- 108*c*: R filter
- 109: outer Filter
- 109*a*: B1 filter
- 109*b*: B2 filter
- 109*c*: G filter
- 109*d*: R filter
- 200: blood vessel density image generation unit
- 202: calculation image signal generation unit
- 204: specific depth blood vessel enhanced image generation unit
- 206: image generation unit

What is claimed is:

1. An endoscope system comprising:
a processor with a memory, configured to:
perform living body characteristic amount calculation processing in which a living body characteristic amount is calculated on the basis of a measurement multi-frame image obtained by imaging an observation target at different timings;
correct contents of the living body characteristic amount calculation processing;
acquire at least one set of correction multi-frame images by imaging the observation target at the different timings;
calculate a plurality of correction image fluctuation amounts each showing a fluctuation amount from a reference image state with respect to an image state based on each of the correction multi-frame images;
calculate a plurality of temporary correction values on the basis of one of the correction image fluctuation amounts, wherein each of the temporary correction values is a candidate for a measurement correction value to be used for correction;
store the correction image fluctuation amounts and the temporary correction values in association with each other;
calculate a measurement image fluctuation amount showing a fluctuation amount from the reference image state with respect to an image state based on the measurement multi-frame image; and
compare each of the correction image fluctuation amounts stored in the memory with the measurement image fluctuation amount, and selects a temporary correction value, which satisfies a specific condition among the temporary correction values stored in the memory, as the measurement correction value, on the basis of the comparison result,
wherein the temporary correction value that satisfies the specific condition is determined to be a temporary correction value associated with a correction image fluctuation amount nearest to the measurement image fluctuation amount, or the temporary correction value that satisfies the specific condition is determined to be a temporary correction value associated with a correction image fluctuation amount calculated in a case where a fluctuation amount index value falls within a specific range, wherein the processor calculates the fluctuation amount index value from at least one of the correction image fluctuation amounts and the measurement image fluctuation amount.

2. The endoscope system according to claim 1,
wherein the fluctuation amount index value is a difference between at least one of the correction image fluctuation amount and the measurement image fluctuation amount or a ratio between at least one of the correction image fluctuation amount and the measurement image fluctuation amount.

3. The endoscope system according to claim 1,
wherein the processor determines a predetermined default temporary correction value as the measurement correction value in a case where there is no temporary correction value that satisfies the specific condition.

4. The endoscope system according to claim 2,
wherein the processor determines a predetermined default temporary correction value as the measurement correction value in a case where there is no temporary correction value that satisfies the specific condition.

5. The endoscope system according to claim 1,
wherein the processor calculates a fluctuation amount in a correction image fluctuation amount calculation region in the correction multi-frame image as one of the correction image fluctuation amounts, and
wherein the processor calculates a fluctuation amount in a measurement image fluctuation amount calculation region in the measurement multi-frame image as the measurement image fluctuation amount.

6. The endoscope system according to claim 4,
wherein the processor calculates a fluctuation amount in a correction image fluctuation amount calculation region in the correction multi-frame image as one of the correction image fluctuation amounts, and
wherein the processor calculates a fluctuation amount in a measurement image fluctuation amount calculation region in the measurement multi-frame image as the measurement image fluctuation amount.

7. The endoscope system according to claim 5,
wherein the processor performs comparison between the correction image fluctuation amount and the measurement image fluctuation amount in a region where the correction image fluctuation amount calculation region and the measurement image fluctuation amount calculation region overlap each other.

8. The endoscope system according to claim 6,
wherein the processor performs comparison between the correction image fluctuation amount and the measurement image fluctuation amount in a region where the correction image fluctuation amount calculation region and the measurement image fluctuation amount calculation region overlap each other.

9. The endoscope system according to claim 1,
wherein the processor calculates the correction image fluctuation amounts, respectively, for a plurality of types of fluctuation factors that cause fluctuation with respect to the reference image state,
wherein the processor calculates measurement image fluctuation amounts, respectively, for the plurality of types of fluctuation factors that cause fluctuation with respect to the reference image state, and
wherein the processor compares the correction image fluctuation amounts with the measurement image fluctuation amounts for each type of fluctuation factor.

10. The endoscope system according to claim 8,
wherein the processor calculates the correction image fluctuation amounts, respectively, for a plurality of types of fluctuation factors that cause fluctuation with respect to the reference image state,
wherein the processor calculates measurement image fluctuation amounts, respectively, for the plurality of types of fluctuation factors that cause fluctuation with respect to the reference image state, and
wherein the processor compares the correction image fluctuation amounts with the measurement image fluctuation amounts for each type of fluctuation factor.

11. The endoscope system according to claim 9,
wherein the fluctuation factors are a positional shift between the correction multi-frame images, a positional shift between the measurement multi-frame images, movements within the correction multi-frame image, a movement within the measurement multi-frarre image, a change in a light emission amount of illumination light in a case where the correction multi-frame images are acquired, a change in a light emission amount of illumination light in a case where the measurement multi-frame image is acquired, changes in pixel values of the correction multi-frame images, changes in pixel values of the measurement multi-frarre images, a change in the amount of a residual liquid in the correction multi-frame images, or a change in the amount of a residual liquid in the measurement multi-frame image.

12. The endoscope system according to claim 10, wherein the fluctuation factors are a positional shift between the correction multi-frame images, a positional shift between the measurement multi-frame images, movements within the correction multi-frame image, a movement within the measurement multi-frarre image, a change in a light emission amount of illumination light in a case where the correction multi-frame images are acquired, a change in a light emission amount of illumination light in a case where the measurement multi-frame image is acquired, changes in pixel values of the correction multi-frame images, changes in pixel values of the measurement multi-frarre images, a change in the amount of a residual liquid in the correction multi-frame images, or a change in the amount of a residual liquid in the measurement multi-frame image.

13. The endoscope system according to claim 1, wherein the processor performs at least any of correction of a calculation table to be used for the calculation of the living body characteristic amount, correction based on the measurement multi-frame image, or correction of the living body characteristic amount, as the correction of the contents of the living body characteristic amount calculation processing.

14. The endoscope system according to claim 7, wherein the processor performs at least any of correction of a calculation table to be used for the calculation of the living body characteristic amount, correction based on the measurement multi-frame image, or correction of the living body characteristic amount, as the correction of the contents of the living body characteristic amount calculation processing.

15. An endoscope system comprising:
a processor with a memory, configured to:
  perform living body characteristic amount calculation processing in which a living body characteristic amount is calculated on the basis of a measurement multi-frame image obtained by imaging an observation target at different timings;
  correct contents of the living body characteristic amount calculation processing;
  acquire at least one set of correction multi-frame images by imaging the observation target at the different timings;
calculate a plurality of correction image fluctuation amounts each showing a fluctuation amount from a reference image state with respect to an image state based on each of the correction multi-frame images;
  calculate a plurality of temporary correction values on the basis of the correction image fluctuation amounts, wherein each of the temporary correction values is a candidate for a measurement correction value to be used for correction;
  store the correction image fluctuation amounts and the temporary correction values in association with each other;
calculate a measurement image fluctuation amount showing a fluctuation amount from the reference image state with respect to an image state based on the measurement multi-frame image; and
  compare each of the correction image fluctuation amounts stored in the memory with the measurement image fluctuation amount, and selects a temporary correction value, which satisfies a specific condition among the temporary correction values stored in the memory, as the measurement correction value, on the basis of the comparison result,
wherein the processor calculates a fluctuation amount index value from the correction image fluctuation amount and the measurement image fluctuation amount, and determines a temporary correction value, which satisfies the specific condition and is associated with a correction image fluctuation amount calculated in a case where the fluctuation amount index value falls within a specific range, as the measurement correction value,
wherein the fluctuation amount index value is a difference between the correction image fluctuation amount and the measurement image fluctuation amount or a ratio between the correction image fluctuation amount and the measurement image fluctuation amount,
wherein the processor determines a predetermined default temporary correction value as the measurement correction value in a case where there is no temporary correction value that satisfies the specific condition,
wherein the processor calculates a fluctuation amount in a correction image fluctuation amount calculation region in the correction multi-frame image as the correction image fluctuation amount,
wherein the processor calculates a fluctuation amount in a measurement image fluctuation amount calculation region in the measurement multi-frame image as the measurement image fluctuation amount,
wherein the processor performs comparison between the correction image fluctuation amount and the measurement image fluctuation amount in a region where the correction image fluctuation amount calculation region and the measurement image fluctuation amount calculation region overlap each other,
wherein the processor calculates correction image fluctuation amounts, respectively, for a plurality of types of fluctuation factors that cause fluctuation with respect to the reference image state,
wherein the processor calculates measurement image fluctuation amounts, respectively, for the plurality of types of fluctuation factors that cause fluctuation with respect to the reference image state,
wherein the processor compares the correction image fluctuation amounts with the measurement image fluctuation amounts for each type of fluctuation factor, and
wherein the fluctuation factors are a positional shift between the correction multi-frame images, a positional shift between the measurement multi-frame images, movements within the correction multi-frame image, a movement within the measurement multi-frarre image, a change in a light emission amount of illumination light in a case where the correction multi-frame images are acquired, a change in a light emission amount of illumination light in a case where the measurement multi-frame image is acquired, changes in pixel values of the correction multi-frame images, changes in pixel values of the measurement multi-frarre images, a change in the amount of a residual liquid in the correction multi-frame images, or a change in the amount of a residual liquid in the measurement multi-frame image.

16. An endoscope system operating method comprising:

performing living body characteristic amount calculation processing in which a living body characteristic amount is calculated on the basis of a measurement multi-frame image obtained by imaging an observation target at different timings;

correcting contents of the living body characteristic amount calculation processing;

acquiring at least one set of correction multi-frame images by imaging the observation target at the different timings;

calculating a plurality of correction image fluctuation amounts each showing a fluctuation amount from a reference image state with respect to an image state based on each of the correction multi-frame images;

calculating a plurality of temporary correction values on the basis of the correction image fluctuation amounts, wherein each of the temporary correction values is a candidate for a measurement correction value to be used for correction;

storing the correction image fluctuation amounts and the temporary correction values in association with each other;

calculating a measurement image fluctuation amount showing a fluctuation amount from the reference image state with respect to an image state based on the measurement multi-frame image; and comparing each of the stored correction image fluctuation amounts with the measurement image fluctuation amount, and selecting a temporary correction value, which satisfies a specific condition among the stored temporary correction values, as the measurement correction value, on the basis of the comparison result, wherein the temporary correction value that satisfies the specific condition is determined to be a temporary correction value associated with a correction image fluctuation amount nearest to the measurement image fluctuation amount, or the temporary correction value that satisfies the specific condition is determined to be a temporary correction value associated with a correction image fluctuation amount calculated in a case where a fluctuation amount index value falls within a specific range, wherein the processor calculates the fluctuation amount index value from at least one of the correction image fluctuation amounts and the measurement image fluctuation amount.

* * * * *